United States Patent [19]

Gordon et al.

[11] Patent Number: 4,500,518
[45] Date of Patent: Feb. 19, 1985

[54] AMINO THIOL DIPEPTIDES

[75] Inventors: Eric M. Gordon, Pennington; Jollie D. Godfrey, Jr., Lawrenceville, both of N.J.

[73] Assignee: E. R. Squibb & Sons, Inc., Princeton, N.J.

[21] Appl. No.: 602,030

[22] Filed: Apr. 19, 1984

[51] Int. Cl.³ .................... H61K 37/00; A01N 43/50; A01N 43/36; C07D 231/00; C07D 211/60; C07D 217/00; C07C 103/52
[52] U.S. Cl. ........................ 514/2; 546/245; 546/146; 548/180; 548/470; 548/356; 548/492; 260/112.5 R
[58] Field of Search ............... 260/112.5 R; 424/177, 424/273 R, 274; 546/245, 146; 548/180, 470, 356, 492

[56] References Cited

U.S. PATENT DOCUMENTS

| 4,329,473 | 5/1982 | Almquist et al. | 546/281 |
| 4,374,829 | 2/1983 | Harris et al. | 424/177 |
| 4,470,973 | 9/1984 | Natarajan et al. | 424/177 |

FOREIGN PATENT DOCUMENTS 897327  1/1984  Belgium .

0050800  5/1982  European Pat. Off. ..... 260/112.5 R

OTHER PUBLICATIONS

Meyer et al., "Angiotensin Converting Enzyme Inhibitors . . . " J. Med. Chem., vol. 25, pp. 996-999 (1982).

Primary Examiner—Delbert R. Phillips
Attorney, Agent, or Firm—Lawrence S. Levinson; Stephen B. Davis

[57] ABSTRACT

Amino thiol substituted dipeptides of the formula

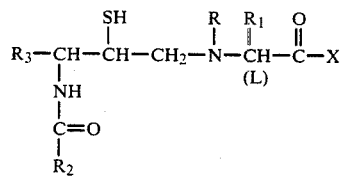

are disclosed. These compounds are useful as hypotensive agents due to their angiotensin converting enzyme inhibition activity and depending upon the definition of X may also be useful as analgesics due to their enkephalinase inhibition activity.

18 Claims, No Drawings

AMINO THIOL DIPEPTIDES

BACKGROUND OF THE INVENTION

Natarajan et al. in Belgian Patent No. 897,327 disclose amino ketone dipeptides of the formula

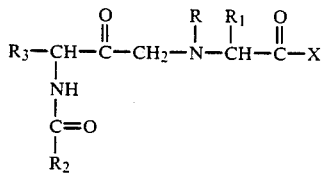

wherein $R_1$ is hydrogen only when R is other than hydrogen.

Gordon et al. in U.S. Ser. No. 515,729 filed July 21, 1983 disclose hydroxy substituted dipeptides of the formula

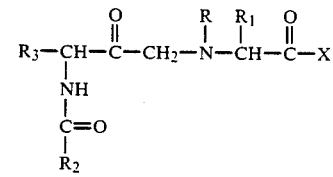

which are prepared by treating the corresponding keto compound with a reducing agent.

Meyer et al., "Angiotensin Converting Enzyme Inhibitors: Modifications of A Tripeptide Analogue", J. Med. Chem., 1982, 25, 996–999, disclose the synthesis and angiotensin converting enzyme inhibition activity of compounds of the formula

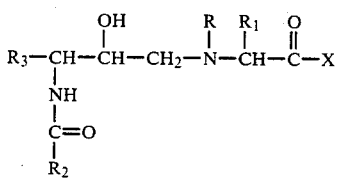

wherein X can be NH and R can be L-proline.

Almquist et al. in U.S. Pat. No. 4,329,473 disclose oxoalkanoic acid derivatives of L-proline as angiotensin converting enzyme inhibitors.

SUMMARY OF THE INVENTION

This invention is directed to the amino thiol dipeptide compounds of formula I and salts thereof

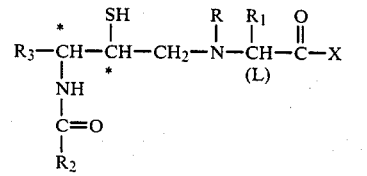

X is an amino or imino acid of the formula

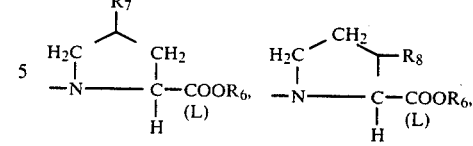

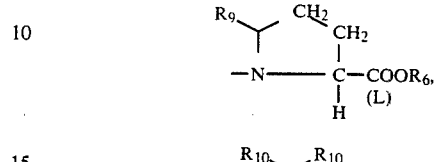

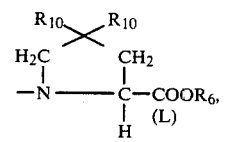

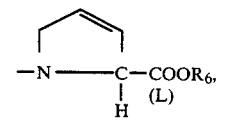

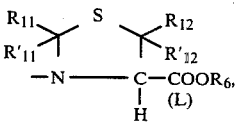

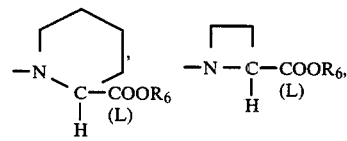

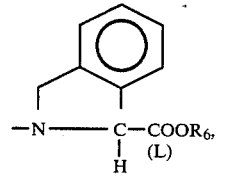

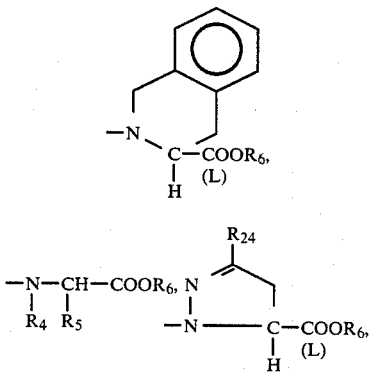

-continued
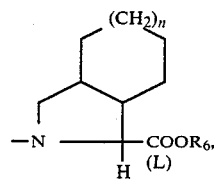
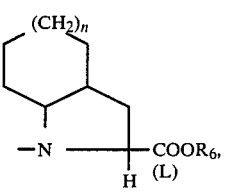
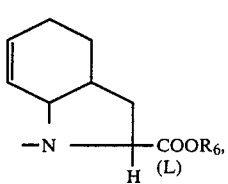
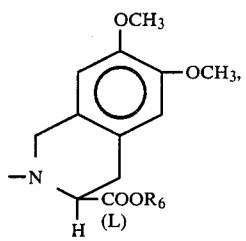
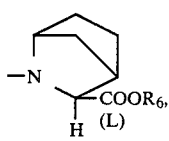
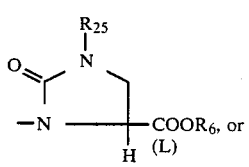
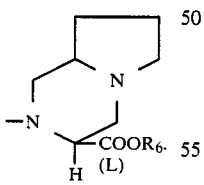
n is zero, one, or two.
R$_{25}$ is lower alkyl of 1 to 4 carbons
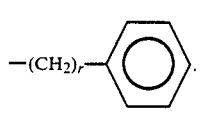
R$_7$ is hydrogen, lower alkyl, halogen, hydroxy,
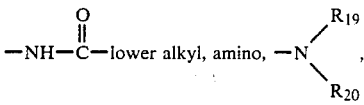
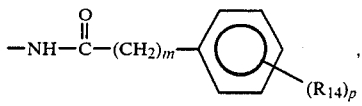
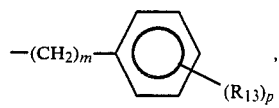
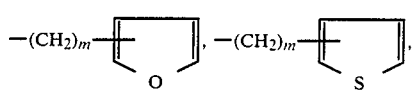
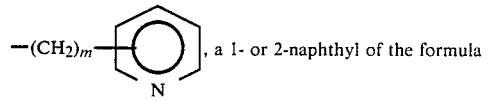
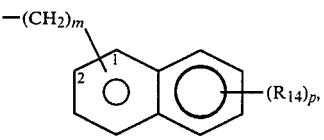
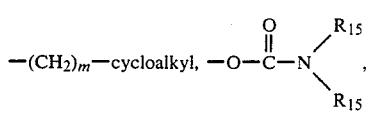
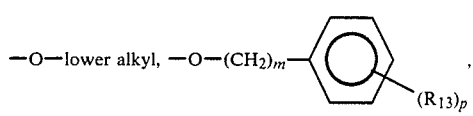
a 1- or 2-naphthyloxy of the formula
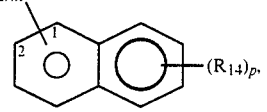
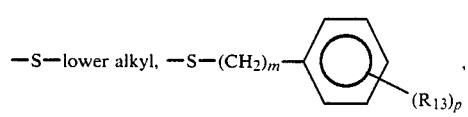
or a 1- or 2-naphthylthio of the formula
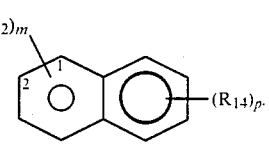
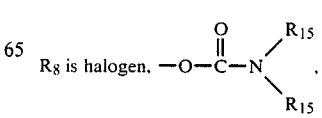
R$_8$ is halogen, -continued

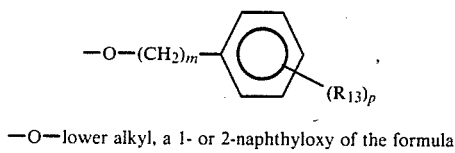

—O—lower alkyl, a 1- or 2-naphthyloxy of the formula

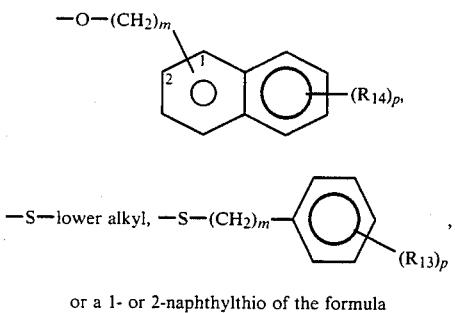

—S—lower alkyl, 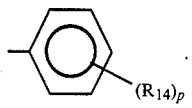, or a 1- or 2-naphthylthio of the formula

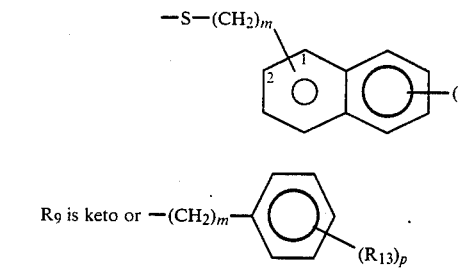

$R_9$ is keto or 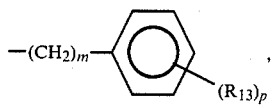

$R_{10}$ is halogen or —Y—$R_{16}$.

$R_{11}$, $R'_{11}$, $R_{12}$ and $R'_{12}$ are independently selected from hydrogen and lower alkyl or $R'_{11}$, $R_{12}$ and $R'_{12}$ are hydrogen and $R_{11}$ is

[structure with $(R_{14})_p$]

$R_{13}$ is hydrogen, lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenoxy, phenylthio, or phenylmethyl.

$R_{14}$ is hydrogen, lower alkyl of 1 to 4 carbons, lower alkoxy of 1 to 4 carbons, lower alkylthio of 1 to 4 carbons, chloro, bromo, fluoro, trifluoromethyl, or hydroxy.

m is zero, one, two, three, or four.

p is one, two or three provided that p is more than one only if $R_{13}$ or $R_{14}$ is hydrogen, methyl, methoxy, chloro, or fluoro.

$R_{15}$ is hydrogen or lower alkyl of 1 to 4 carbons.

Y is oxygen or sulfur.

$R_{16}$ is lower alkyl of 1 to 4 carbons,

[structure —(CH2)m—phenyl—$(R_{13})_p$]

or the $R_{16}$ groups join to complete an unsubstituted 5- or 6-membered ring or said ring in which one or more of the carbons has a lower alkyl of 1 to 4 carbons or a di(lower alkyl of 1 to 4 carbons) substituent.

$R_4$ is hydrogen, lower alkyl,

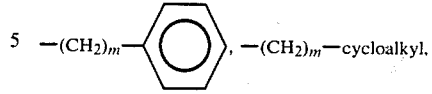

, 

$R_5$ is hydrogen, lower alkyl, 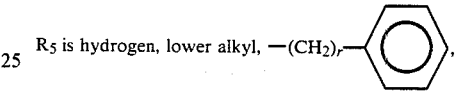

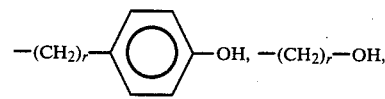

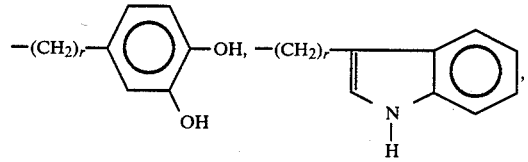

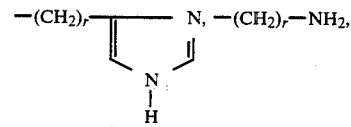

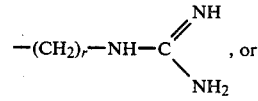, or

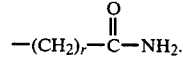

r is an integer from 1 to 4.

$R_{19}$ is lower alkyl, benzyl, or phenethyl.

$R_{20}$ is hydrogen, lower alkyl, benzyl or phenethyl.

R is hydrogen, lower alkyl, cycloalkyl,

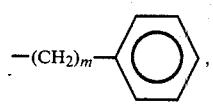,

—(CH2)2—NH2,   —(CH2)3—NH2,   —(CH2)4—NH2,
—(CH2)2—OH,    —(CH2)3—OH,    —(CH2)4—OH,
—(CH2)2—SH,    —(CH2)3—SH, or —(CH2)4—SH.

$R_1$ is hydrogen, lower alkyl, halo substituted lower alkyl,

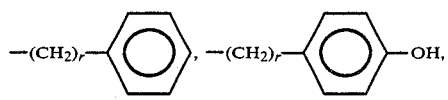

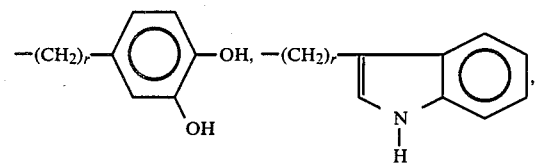

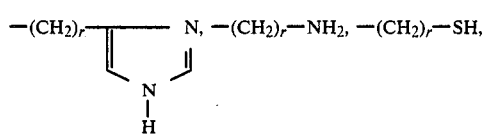

—$(CH_2)_r$—OH, —$(CH_2)_r$—S—lower alkyl,

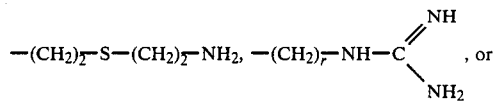

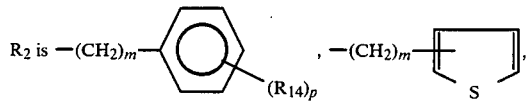

$R_2$ is 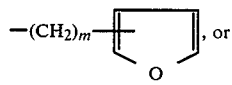

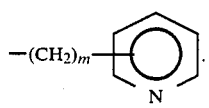

$R_3$ is hydrogen, lower alkyl, 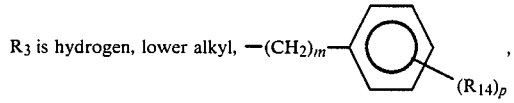

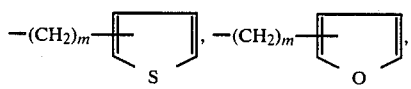

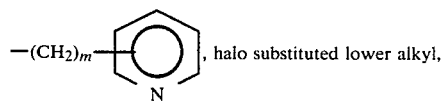, halo substituted lower alkyl,

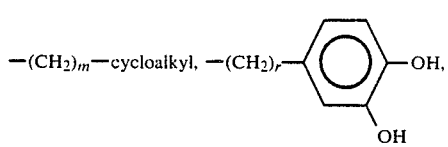

-continued

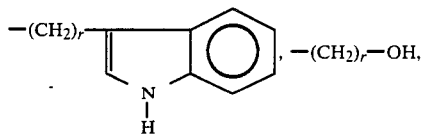

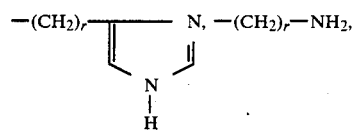

—$(CH_2)_r$—SH, —$(CH_2)_r$—S—lower alkyl,

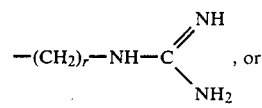

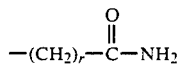

wherein m, $R_{14}$, p and r are as defined above.

$R_6$ is hydrogen, lower alkyl, p-methoxybenzyl, benzhydryl,

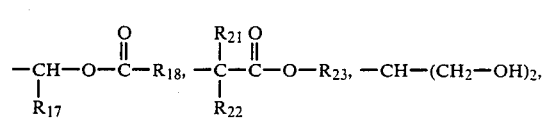

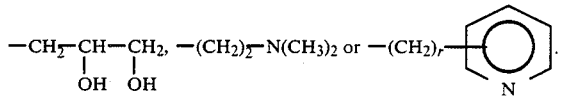

$R_{17}$ is hydrogen, lower alkyl, cycloalkyl, or phenyl.
$R_{18}$ is hydrogen, lower alkyl, lower alkoxy, or phenyl or $R_{17}$ and $R_{18}$ taken together are —$(CH_2)_2$—, —$(CH_2)_3$—, —CH=CH—, or

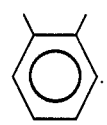

$R_{21}$ and $R_{22}$ are independently selected from hydrogen and lower alkyl.
$R_{23}$ is lower alkyl.
$R_{24}$ is hydrogen, lower alkyl,

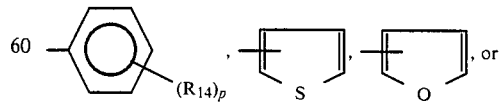

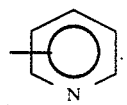

DETAILED DESCRIPTION OF THE INVENTION

This invention in its broadest aspects relates to the amino thiol dipeptide compounds of formula I above, intermediates useful in the preparation of such compounds, compositions containing such compounds and the method of using such compounds as pharmaceutical agents.

The term lower alkyl used in defining various symbols refers to straight or branched chain radicals having up to seven carbons. The preferred lower alkyl groups are up to four carbons with methyl and ethyl most preferred similarly the terms lower alkoxy and lower alkylthio refer to such lower alkyl groups attached to an oxygen or sulfur.

The term cycloalkyl refers to saturated rings of 3 to 7 carbon atoms with cyclopentyl and cyclohexyl being most preferred.

The term halogen refers to chloro, bromo and fluoro.

The term halo substituted lower alkyl refers to such lower alkyl groups described above in which one or more hydrogens have been replaced by chloro, bromo or fluoro groups such as trifluoromethyl, which is preferred, pentafluoroethyl, 2,2,2-trichloroethyl, chloromethyl, bromomethyl, etc.

The symbols

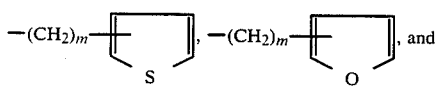, 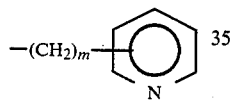, and

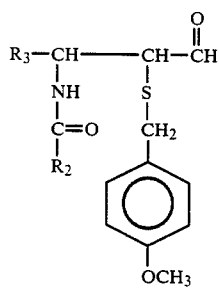

represent that the alkylene bridge is attached to an available carbon atom.

The compounds of formula I can be prepared according to the following procedure. An aldehyde of the formula

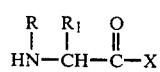 (II)

is reductively coupled with a dipeptide ester of the formula $$\begin{array}{ccc} R & R_1 & O \\ | & | & \| \\ HN-CH-C-X \end{array}$$ (III)

wherein $R_6$ in the definition of X is an acid cleavable protecting group such as t-butyl, benzhydryl, or p-methoxybenzyl.

The resulting p-methoxybenzyl protected compound of the formula

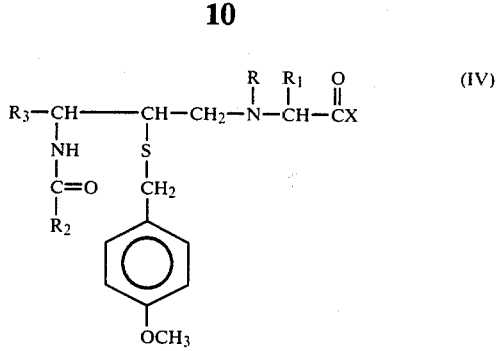 (IV)

is treated with trifluoroacetic acid and anisole to remove the $R_6$ ester group and mercuric trifluoroacetate acid to remove the p-methoxybenzyl sulfur protecting group and give the amino thiol product of formula I.

The aldehyde intermediate of formula II can be prepared as follows. An N-protected carboxylic acid of the formula

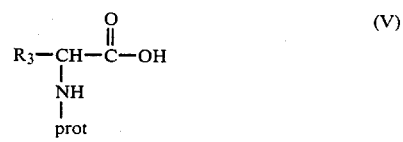 (V)

wherein prot is a protecting group such as benzyloxycarbonyl is treated with diazomethane in the presence of N-methylmorpholine and isobutylchloroformate to yield

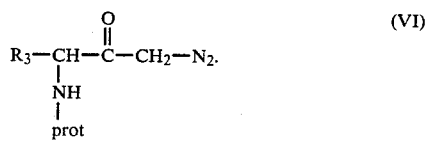 (VI)

The diazo compound of formula VI in methanol is treated with silver benzoate and triethylamine to yield the methyl ester of the formula

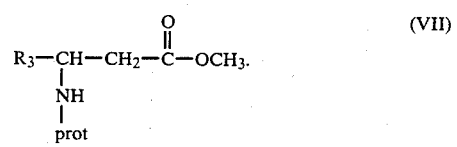 (VII)

Removal of the N-protecting group such as by hydrogenation followed by reaction with the acid chloride of the formula

 (VIII)

yields the methyl ester of the formula

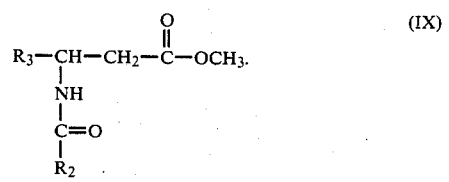 (IX)

The methyl ester of formula IX is treated with lithium diisopropylamine and the disulfide of the formula

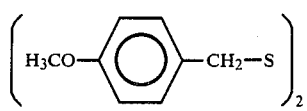  (X)

at low temperature to yield the protected sulfide of the formula

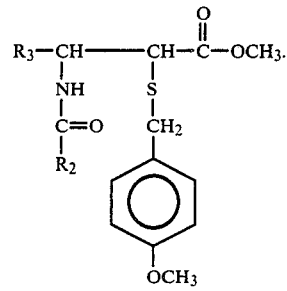  (XI)

The methyl ester of formula XI is treated with lithium chloride and sodium borohydride to yield the alcohol of the formula

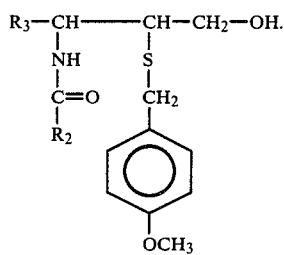  (XII)

The alcohol of formula XII is treated with pyridinium-1-sulfonate and dimethylsulfoxide in the presence of diisopropylethylamine to yield the aldehyde of formula II.

The dipeptides of formula III are described in the literature. They can be obtained by reacting the N-protected amino acid of the formula

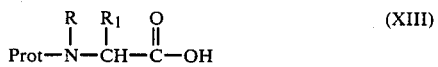  (XIII)

wherein the N-protecting group is benzyloxycarbonyl, t-butoxycarbonyl, or p-methoxybenzyloxycarbonyl with the imino or amino acid ester of the formula

H—X.  (XIV)

Removal of the N-protecting group yields the intermediate of formula III. When the imino or amino acid of formula XIV is known in the acid form it can be readily converted to the ester by conventional means. For example, the esters where $R_6$ is t-butyl can be obtained by treating the corresponding N-carbobenzyloxy imino or amino acid with isobutylene under acidic conditions and then removing the N-carbobenzyloxy protecting group by catalytic hydrogenation.

In the above reactions if any or all of R, $R_1$, $R_3$ and $R_5$ are

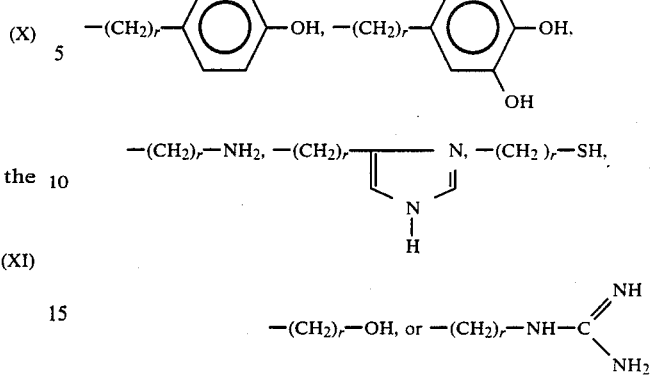

then the hydroxyl, amino, imidazolyl, mercaptan or guanidinyl function should be protected during the reaction. Suitable protecting groups include benzyloxycarbonyl, t-butoxycarbonyl, benzyl, benzhydryl, trityl, etc., and nitro in the case of guanidinyl. The protecting group is removed by hydrogenation, treatment with acid, or other known methods following completion of the reaction.

The ester products of formula I wherein $R_6$ is

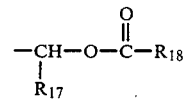

may be obtained by employing the dipeptide of formula III in the above reactions with such ester group already in place. Such ester reactants can be prepared by treating the dipeptide of formula III wherein $R_6$ is hydrogen with an acid chloride such as

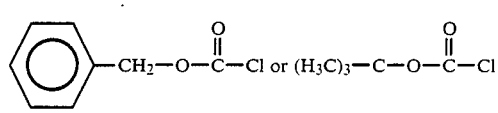

so as to protect the N-atom. The protected compound is then reacted in the presence of a base with a compound of formula

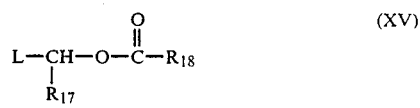  (XV)

wherein L is a leaving group such as chlorine, bromine, tolylsulfonyl, etc., followed by removal of the N-protecting group such as by treatment with acid or hydrogenation.

The ester products of formula I wherein $R_6$ is

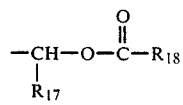

can also be obtained by treating the product of formula I wherein $R_6$ is hydrogen with a molar excess of the compound of formula XV.

The ester products of formula I wherein $R_6$ is $$-\underset{\underset{R_{22}}{|}}{\overset{\overset{R_{21}}{|}}{C}}-\overset{\overset{O}{\|}}{C}-O-R_{23}$$

can be prepared by treating the product of formula I wherein $R_6$ is hydrogen with a molar excess of the compound of the formula $$I-\underset{\underset{R_{22}}{|}}{\overset{\overset{R_{21}}{|}}{C}}-\overset{\overset{O}{\|}}{C}-O-R_{23}. \quad (XVI)$$

The ester products of formula I wherein $R_6$ is $-CH-(CH_2-OH)_2$ or $$-CH_2-\underset{\underset{OH}{|}}{CH}-\underset{\underset{OH}{|}}{CH_2}$$

can be prepared by coupling the product of formula I wherein $R_6$ is hydrogen with a molar excess of the compound of the formula $$\underset{\underset{OH}{|}}{CH}-(CH_2-OProt)_2 \quad (XVII)$$

or the formula $$\underset{\underset{OH}{|}}{CH_2}-\underset{\underset{OProt}{|}}{CH}-\underset{\underset{OProt}{|}}{CH_2} \quad (XVIII)$$

in the presence of a coupling agent such as dicyclohexylcarbodiimide followed by removal of the hydroxyl protecting groups.

Similarly, the ester products of formula I wherein $R_6$ is $-(CH_2)_2-N(CH_3)_2$ or $$-CH_2-\underset{N}{\underset{\|}{\bigcirc}}$$

can be prepared by coupling the product of formula I wherein $R_6$ is hydrogen with a molar excess of the compound of the formula $$HO-CH_2-CH_2-N-(CH_3)_2 \quad (XIX)$$

or the formula $$HO-(CH_2)_r-\underset{N}{\underset{\|}{\bigcirc}} \quad (XX)$$

in the presence of a coupling agent such as dicyclohexylcarbodiimide.

The products of formula I wherein $R_7$ is amino may be obtained by reducing the corresponding products of formula I wherein $R_7$ is azido.

Preferred compounds of this invention with respect to the peptide part of the structure of formula I are those wherein:

R is hydrogen or straight or branched chain lower alkyl of 1 to 4 carbons.

$R_1$ is hydrogen, straight or branched chain lower alkyl or 1 to 4 carbons, $-CF_3$, $-(CH_2)_r-NH_2$ wherein r is an integer from 1 to 4, $-CH_2-\bigcirc$, $-CH_2-\bigcirc-OH$, $-CH_2-\bigcirc\overset{OH}{\underset{OH}{}}$, $-CH_2-\underset{\underset{H}{N}}{\bigcirc}$, $-CH_2-\underset{\underset{H}{N}}{\overset{}{\bigcirc}}N$, $-CH_2-SH$, $-(CH_2)_2-S-(CH_2)_2-NH_2$, $-(CH_2)_2-S-CH_3$, $-(CH_2)_3NHC\overset{NH}{\underset{NH_2}{\diagup}}$, $-CH_2-OH$, $-CH_2-\overset{O}{\overset{\|}{C}}-NH_2$, or $-(CH_2)_2-\overset{O}{\overset{\|}{C}}-NH_2$.

$R_4$ is hydrogen, cyclohexyl or phenyl.

$R_5$ is hydrogen, straight or branched chain lower alkyl of 1 to 4 carbons, $-CH_2-\bigcirc$, $-CH_2-\bigcirc-OH$, $-CH_2-\bigcirc\overset{OH}{\underset{OH}{}}$, $-CH_2-\underset{\underset{H}{N}}{\bigcirc}$, $-CH_2-\underset{\underset{H}{N}}{\overset{}{\bigcirc}}N$, $-(CH_2)_4-NH_2$, $-CH_2-SH$, $-(CH_2)_2-S-CH_3$, $-(CH_2)_3NHC\overset{NH}{\underset{NH_2}{\diagup}}$, $-CH_2-\overset{O}{\overset{\|}{C}}-NH_2$ or $-(CH_2)_2-\overset{O}{\overset{\|}{C}}-NH_2$.

$R_6$ is hydrogen, straight or branched chain lower alkyl of 1 to 4 carbons, alkali metal salt,

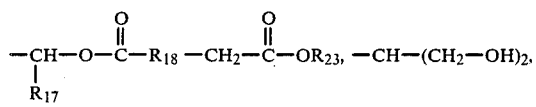, $-CH-(CH_2-OH)_2$,

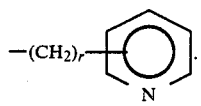

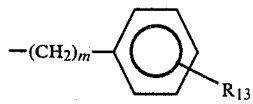

r is an integer from 1 to 4.

$R_{23}$ is straight or branched chain lower alkyl of 1 to 4 carbons, especially $-C(CH_3)_3$.

$R_{17}$ is hydrogen, straight or branched chain lower alkyl of 1 to 4 carbons, or cyclohexyl.

$R_{18}$ is straight or branched chain lower alkyl of 1 to 4 carbons or phenyl.

$R_7$ is hydrogen.

$R_7$ is hydroxy.

$R_7$ is straight or branched chain lower alkyl of 1 to 4 carbons or cyclohexyl.

$R_7$ is amino.

$R_7$ is —O—lower alkyl wherein lower alkyl is straight or branched chain of 1 to 4 carbons.

$R_7$ is

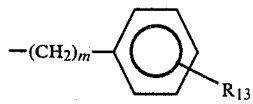

wherein m is zero, one or two and $R_{13}$ is hydrogen, methyl, methoxy, methylthio, chloro, bromo, fluoro, or hydroxy.

$R_7$ is

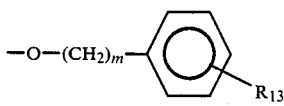, 1-naphthyloxy or 2-naphthyloxy wherein m is zero, one, or two and $R_{13}$ is hydrogen, methyl, methoxy, methylthio, chloro, bromo, fluoro, or hydroxy.

$R_7$ is —S—lower alkyl wherein lower alkyl is straight or branched chain of 1 to 4 carbons.

$R_7$ is

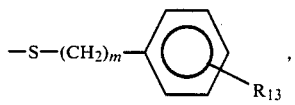, 1-naphthylthio, or 2-naphthylthio wherein m is zero, one, or two and $R_{13}$ is hydrogen, methyl, methoxy, methylthio, chloro, bromo, fluoro, or hydroxy.

$R_8$ is —O—lower alkyl wherein lower alkyl is straight or branched chain of 1 to 4 carbons.

$R_8$ is

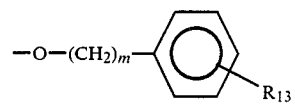

wherein m is zero, one, or two and $R_{13}$ is hydrogen, methyl, methoxy, methylthio, chloro, bromo, fluoro, or hydroxy.

$R_8$ is —S—lower alkyl wherein lower alkyl is straight or branched chain of 1 to 4 carbons.

$R_8$ is

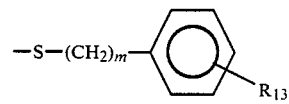

wherein m is zero, one or two and $R_{13}$ is hydrogen, methyl, methoxy, methylthio, chloro, bromo, fluoro or hydroxy.

$R_9$ is phenyl, 2-hydroxyphenyl, or 4-hydroxyphenyl.

$R_{10}$ are both fluoro or chloro.

$R_{10}$ are both $-Y-R_{16}$ wherein Y is O or S, $R_{16}$ is straight or branched chain lower alkyl of 1 to 4 carbons or the $R_{16}$ groups join to complete an unsubstituted 5- or 6-membered ring or said ring in which one or more of the available carbons has a methyl or dimethyl substituent.

$R_{11}$, $R_{11}'$, $R_{12}$ and $R_{12}'$ are all hydrogen, or $R_{11}$ is phenyl, 2-hydroxyphenyl, or 4-hydroxyphenyl and $R_{11}'$, $R_{12}$ and $R_{12}'$ are hydrogen.

$R_{24}$ is phenyl.

Most preferred compounds of this invention with respect to the peptide part of the structure of formula I are those wherein:

X is 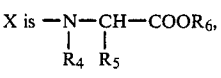, 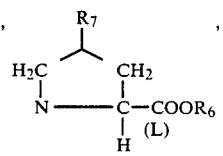

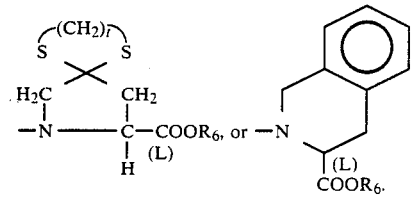

R is hydrogen or methyl.

$R_1$ is hydrogen, methyl, or $-(CH_2)-_4NH_2$.

$R_6$ is hydrogen, straight or branched chain lower alkyl of 1 to 4 carbons, or an alkali metal salt.

$R_4$ is cyclohexyl or phenyl and $R_5$ is hydrogen.

$R_4$ is hydrogen and $R_5$ is methyl,

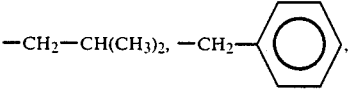

-continued

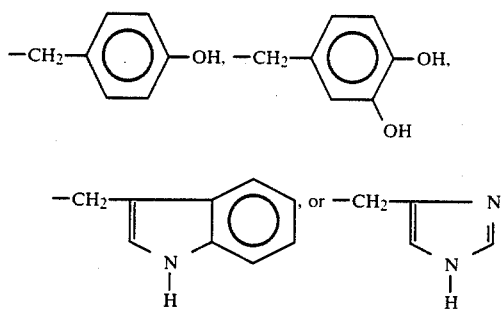

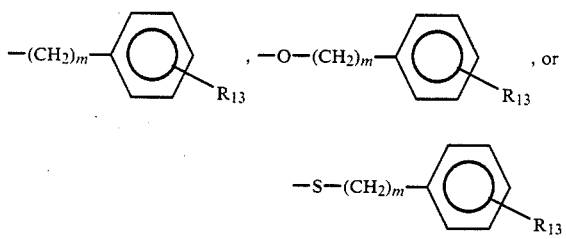

$R_7$ is hydrogen, cyclohexyl, lower alkoxy of 1 to 4 carbons,

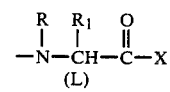

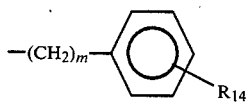

wherein m is zero, one, or two and $R_{13}$ is hydrogen, methyl, methoxy, methylthio, Cl, Br, F, or hydroxy, especially preferred wherein $R_7$ is hydrogen.

t is two or three, especially where t is two.

Preferred compounds of this invention with respect to the thiol substituted portion of the structure of formula I are those wherein:

$R_2$ is

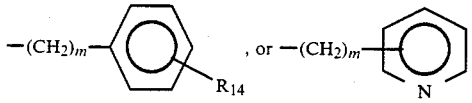

wherein m is zero, one, or two and $R_{14}$ is hydrogen, methyl, methoxy, methylthio, Cl, Br, F, or hydroxy, especially phenyl.

$R_3$ is straight or branched chain lower alkyl of 1 to 4 carbons, —$(CH_2)_r$—$NH_2$, wherein m is zero, one, or two, $R_{14}$ is hydrogen, methyl, methoxy, methylthio, Cl, Br, F, or hydroxy, and r is an integer from 1 to 4, especially benzyl.

The compounds of formula I wherein $R_6$ is hydrogen form salts with a variety of inorganic or organic bases. The nontoxic, pharmaceutically acceptable salts are preferred, although other salts are also useful in isolating or purifying the product. Such pharmaceutically acceptable salts include metal salts such as sodium, potassium or lithium, alkaline earth metal salts such as calcium or magnesium, and salts derived from amino acids such as arginine, lysine, etc. The salts are obtained by reacting the acid form of the compound with an equivalent of the base supplying the desired ion in a medium in which the salt precipitates or in aqueous medium and then lyophilizing.

Similarly, the compounds of formula I form salts with a variety of inorganic and organic acids. Again, the non-toxic pharmaceutically acceptable salts are preferred, although other salts are also useful in isolating or purifying the product. Such pharmaceutically acceptable salts include those formed with hydrochloric acid, methanesulfonic acid, sulfuric acid, maleic acid, etc. The salts are obtained by reacting the product with an equivalent amount of the acid in a medium in which the salt precipitates.

As shown above, the peptide portion of the molecule of the products of formula I represented by $$-\overset{R}{\underset{|}{N}}-\overset{R_1}{\underset{|}{CH}}-\overset{O}{\underset{\|}{C}}-X$$
(L)

is in the L-configuration ($R_1$ is other than hydrogen). One of two asymmetric centers are also present in the thiol substituted portion of the molecule as represented by the * in formula I. Of course, if $R_3$ is hydrogen, then only one center is present. Thus, the compounds of formula I can exist in diastereoisometric forms or in mixtures thereof. The above described processes can utilize racemates, enantiomers or diastereomers as starting materials. When diastereomeric products are prepared, they can be separated by conventional chromatographic or fractional crystallization methods.

The products of formula I wherein the imino acid ring is monosubstituted give rise to cistrans isomerism. The configuration of the final product will depend upon the configuration of the $R_7$, $R_8$ and $R_9$ substituent in the starting material of formula XIV.

The compounds of formula I, and the pharmaceutically acceptable salts thereof, are hypotensive agents. They inhibit the conversion of the decapeptide angiotensin I to angiotensin II and, therefore, are useful in reducing or relieving angiotensin related hypertension. The action of the enzyme renin or angiotensinogen, a pseudoglubulin in blood plasma, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention intervene in the angiotensinogen→(renin)→angiotensin I→angiotensin II sequence by inhibiting angiotensin converting enzyme and reducing or eliminating the formation of the pressor substance angiotensin II. Thus by administration of a composition containing one (or a combination) of the compounds of this invention, angiotensin dependent hypertension in a species of mammal (e.g., humans) suffering therefrom is alleviated. A single dose, or preferably two or four divided daily doses, provided on a basis of about 0.1 to 100 mg., preferably about 1 to 50 mg., per kg. of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in an effective amount which comprises a total daily dosage of about 30 to 600 mg., preferably about 30 to 330 mg. of a compound of this invention, and about 15 to 300 mg., preferably about 15 to 200 mg. of the diuretic, to a mammalian species in need thereof. Exemplary of the diuretics contemplated for use in combination with a compound of this invention are the thiazide diuretics, e.g., chlorothiazide, hydrochlorothiazide, flumethiazide, hydroflumethiazide, bendroflumethiazide, methyclothiazide, trichloromethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration, or in sterile solutions or suspensions for parenteral administrations. About 10 to 500 mg. of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The compounds of formula I wherein X is

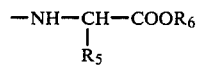

also possess enkephalinase inhibition activity and are useful as analgesic agents. Thus, by the administration of a composition containing one or a combination of such compounds of formula I or a pharmaceutically acceptable salt thereof, pain is alleviated in the mammalian host. A single dose, or preferably two to four divided daily doses, provided on a basis of about 0.1 to about 100 mg. per kilogram of body weight per day, preferably about 1 to about 50 mg. per kilogram per day, produces the desired analgesic activity. The composition is preferably administered orally but parenteral routes such as subcutaneous can also be employed.

The following examples are illustrative of the invention. Temperatures are given in degrees centigrade. LH-20 refers to a Sephadex chromatography gel commercially available from Pharmacia Fine Chemicals.

EXAMPLE 1

1-[N-[(3S)-3-(Benzoylamino)-2-mercapto-4-phenyl-butyl]-L-alanyl]-L-proline (isomer A)

(a) (4-Methoxyphenyl)methyl disulfide

A benzene solution of iodine is added to a stirred mixture of 4-methoxybenzenemethanethiol (25 g., 0.162 mole) in benzene (300 ml.) and water (300 ml.) containing sodium bicarbonate (29.4 g., 0.35 mole) until the color of iodine persists. After stirring for 15 minutes, the excess iodine is quenched with sodium thiosulfate. The benzene fraction is washed with water, aqueous sodium thiosulfate, 1N sodium bicarbonate, and brine. After drying over anhydrous MgSO$_4$, the solvent is removed at reduced pressure to give a brown solid that is washed with ether to give a light tan solid. This material is dissolved in hot ethyl acetate for recrystallization and while cooling the colorless solution turns dark brown which is indicative of iodine. The resulting solution is cooled in an ice bath and the resulting solid is collected by filtration. This solid is then recrystallized from ethyl acetate and washed with ether to give 15.1 g. of (4-methoxyphenyl)methyl disulfide as a colorless solid; m.p. 98°–100°.

Anal. calc'd for $C_{16}H_{18}O_2S_2$: C, 62.71; H, 5.92; S, 20.92 Found: C, 62.60; H, 5.97; S, 20.86.

(b) (S)-3 [(Benzyloxycarbonyl)amino]-1-diazo-4-phenyl-2-butanone

Isobutyl chloroformate (23.4 ml., 180 mmole) is added to a solution of N-benzyloxycarbonyl-L-phenylalanine (53.9 g., 180 mmole) and N-methylmorpholine (19.8 ml., 180 mmole) in dry tetrahydrofuran (250 ml.) at −20° under argon. After stirring for 15 minutes, the N-methylmorpholine hydrochloride is removed by filtration and the filtrate is treated with a cold (0°), etheral solution of diazomethane. The resulting mixture is allowed to warm to room temperature and stirred for 2 hours. The excess diazomethane is removed by bubbling a stream of nitrogen through the reaction mixture for 30 minutes. The solvent is removed at reduced pressure and the residue is dissolved in ethyl acetate. The resulting solution is washed with water (twice), 1N sodium bicarbonate (twice), 0.25 M citric acid (twice), and brine. After drying over anhydrous MgSO$_4$, the solvent is removed at reduced pressure and the residue is dissolved in isopropyl ether. The resulting precipitate is collected by filtration to give 41.07 g. of (S)-3-[(benzyloxycarbonyl)amino]-1-diazo-4-phenyl-2-butanone as a light yellow solid. TLC(silica gel, hexane:ethyl acetate; (3:1) R$_f$=0.12. (c) (S)-β-[Benzyloxycarbonyl)amino]-benzenebutanoic acid, methyl ester To a solution of (S)-3-[(benzyloxycarbonyl)amino]-1-diazo-4-phenyl-2-butanone (10 g., 30.8 mmole) in methanol (100 ml.) is added 0.5 ml. of a solution of silver benzoate (1.0 g.) in triethylamine (12.5 ml.). After nitrogen evolution ceases, an additional 0.5 ml. of the silver benzoate/triethylamine solution is added and stirring continued for an additional 15 minutes. The reaction mixture is treated with activated charcoal and filtered through Celite. The filtrate is concentrated at reduced pressure and the residue is dissolved in ethyl acetate. This solution is washed with water, 1N hydrochloric acid, 1N sodium bicarbonate (twice), and brine. After drying over anhydrous MgSO$_4$, the solvent is removed at reduced pressure and the residue is chromatographed (Florisil, ether) to give 9.43 g. of (S)-β-[(benzyloxycarbonyl)amino]-benzenebutanoic acid, methyl ester as a waxy yellow solid. TLC (silica gel; hexane:ethyl acetatel; 4:1) R$_f$=0.25.

(d) (S)-δ-(Benzoylamino)-benzenebutanoic acid, methyl ester

A mixture of (S)-β-[(benzyloxycarbonyl)amino]-benzenebutanoic acid, methyl ester (10.0 g., 30.5 mmole), p-toluenesulfonic acid monohydrate (5.8 g., 30.5 mmole), and palladium hydroxide carbon catalyst (1.0 g.) in 95% ethanol (170 ml.) is stirred under a hydrogen atmosphere (balloon). The system is evacuated and refilled with fresh hydrogen every 20 minutes. After 1.5 hours, the catalyst is removed by filtration and the filtrate is concentrated at reduced pressure to give a colorless solid.

To a solution of the above colorless solid and diisopropylethylamine (8.23 ml., 47.2 mmole) in anhydrous tetrahydrofuran (150 ml.) at 0° is added benzoyl chloride (6.27 ml., 54 mmole). After stirring for 30 minutes, the mixture is warmed to room temperature and stirring continued for 45 minutes. The reaction mixture is then treated with 1N sodium bicarbonate (150 ml.). After stirring for 30 minutes, the bulk of the tetrahydrofuran is removed at reduced pressure and the residue is extracted with ethyl acetate. The ethyl acetate fraction is washed with water (twice), 1N hydrochloric acid (twice), 1N sodium bicarbonate (twice), and brine. After drying over anhydrous MgSO$_4$, the solvent is removed at reduced pressure and the residue is washed with hexane to give 8.15 g. (S)-β-(benzoylamino)-benzenebutanoic acid, methyl ester as a colorless solid. TLC (silica gel; hexane:ethyl acetate, 1:1) R$_f$=0.38.

(e) (S)-β-(Benzoylamino)-α-[[(4-methoxyphenyl)methyl]thio]-benzenebutanoic acid, methyl ester To a solution of freshly distilled diisopropylamine (2.07 ml., 14.8 mmole) in dry tetrahydrofuran (20 ml.) at 0° under argon is added a hexane solution of n-butyl lithium (6.02 ml. of a 2.4 M solution, 14.5 mmole). After stirring at 0° for 30 minutes, the resulting solution of lithium diisopropylamide is cooled to −78° and a solution of (S)-β-(benzoylamino)-benzenebutanoic acid, methyl ester (2.0 g., 6.72 mmole) in tetrahydrofuran (20 ml.) is added dropwise over a period of 5 minutes. After stirring at −78° for 15 minutes, a solution of (4-methoxyphenyl)methyl disulfide (2.5 g., 8.07 mmole) in tetrahydrofuran (9 ml.) is added. After 5 minutes at −78°, the mixture is warmed to 0° and stirring continued for 45 minutes. The reaction is quenched with 1N hydrochloric acid and diluted with ethyl acetate. The resulting solution is washed with water, 1N hydrochloric acid, 1N sodium bicarbonate, and brine. After drying over anhydrous MgSO$_4$, the solvent is removed at reduced pressure and the residue is flash chromatographed (silica gel LPS-1; benzene:ethyl acetate, 93:7) to give 1.85 g. of pale yellow solid (S)-β-(benzoylamino)-ϵ-[[(4-methoxyphenyl)methyl]thio]-benzenebutanoic acid, methyl ester as a mixture of diastereomers. TLC (silica gel; benzene:ethyl acetate, 9:1) R$_f$=0.29 and 0.26.

(f) (S)-β-(Benzoylamino)-α-[[(4-methoxyphenyl)methyl]thio]-benzenebutanol (isomer A)

Lithium chloride (0.7 g., 4 eq.) and sodium borohydride (0.62 g., 4 eq.) are added to a solution of (S)-β-(benzoylamino)-β-[[(4-methoxyphenyl)methyl]thio]-benzenebutanoic acid, methyl ester (1.85 g., 4.11 mmole) in tetrahydrofuran (25 ml.) and absolute ethanol (25 ml.). After stirring at room temperature for 21 hours, the mixture is quenched with 1N hydrochloric acid and diluted with ethyl acetate. The resulting solution is washed with water, 1N hydrochloric acid, 1N sodium bicarbonate, the brine. After drying over anhydrous MgSO$_4$, the solvent is removed at reduced pressure and the residue flash chromatographed (silica gel LPS-1; benzene:acetone, 91:9) to give the separated diastereomers of (S)-β-(benzoylamino)-α-[[(4-methoxyphenyl)methyl]thio]-benzenebutanol as colorless solids. Isomer A; 0.48 g.; TLC (silica gel; benzene: acetone, 9:1) R$_f$=0.27; and isomer B; 0.52 g.; TLC (silica gel; benzene:acetone, 9:1) R$_f$=0.16.

(g) (S)-β-(Benzoylamino)-β-[[(4-methoxyphenyl)methyl]thio]-benzenebutanal (isomer A)

A mixture of anhydrous dimethylsulfoxide (5 ml.) and pyridinium-1-sulfonate (0.91 g., 5.65 ml.) at room temperature under argon is stirred for 15 minutes and then diluted with dry methylene chloride (5 ml.). To the resulting solution is added a solution of (S)-β-(benzoylamino)-α-[[(4-methoxyphenyl)methyl]thio]-benzenebutanol (isomer A) (0.48 g., 1.13 mmole) and diisopropylethylamine (1.98 ml., 11.3 mmole) in methylene chloride (7 ml.). After stirring for 15 minutes, the mixture is diluted with ethyl acetate and washed with water (twice), 1N sodium bicarbonate (twice), and brine. After drying over anhydrous MgSO$_4$, the solvent is removed at reduced pressure to give 0.45 g. of (S)-β-(benzoylamino)-α-[[(4-methoxyphenyl)methyl]thio]-benzenebutanal (isomer A) as a pale yellow solid. TLC (silica gel; benzene:acetone, 9:1) R$_f$=0.44.

(h) 1-[N-[(3S)-3-(Benzoylamino)-2-[[(4-methoxyphenyl)methyl]thio]-4-phenylbutyl]-L-alanyl]-L-proline, 1,1-dimethylethyl ester (isomer A)

A mixture of (S)-β-(benzoylamino)-α-[[(4-methoxyphenyl)methyl]thio]-benzenebutanal (isomer A) (0.45 g., 1.07 mmole), L-alanyl-L-proline, 1,1-dimethylethyl ester (0.78 g., 3.21 mmole), and crushed 3A° molecular sieves (2 g.) in tetrahydrofuran (5 ml.) and absolute ethanol (5 ml.) is stirred at room temperature under argon. After 2.5 hours, sodium cyanoborohydride (0.20 g., 3 eq.) is added and stirring continued for 15 hours. The reaction mixture is filtered to remove the sieves and the filtrate is diluted with ethyl acetate and washed with water, 1N hydrochloric acid (twice), 1N sodium bicarbonate, and brine. After drying over anhydrous MgSO$_4$, the solvent is removed to give the desired product, as a mixture of diastereomers, as a pale yellow oil. TLC (silica gel, benzene:acetone, 4:1) isomer A at R$_f$=0.30 and isomer B at R$_f$=0.13. Flash chromatography (silica gel LPS-1; benzene:acetone, 7:3) affords impure product (isomer A). Repeated flash chromatography (silica gel LPS-1; ethyl acetate:benzene, 6:4) gives 0.20 g. of 1-[N-[(3S)-3-(benzoylamino)- 2-[[(4-methoxyphenyl)methyl]thio]-4-phenylbutyl]L-alanyl]-L-proline, 1,1-dimethylethyl ester (isomer A) as a nearly colorless oil.

(i) 1-[N-[(3S)-3-(Benzoylamino)-2-mercapto-4-phenylbutyl]-L-alanyl]-L-proline (isomer A)

A solution of the 1,1-dimethylethyl ester product from part (h) (0.57 g., 0.88 mmole) and anisole (1.0 ml.) in trifluoroacetic acid (19 ml.) is stirred at room temperature for 1 hour. After cooling to 0°, mercuric trifluoroacetate (376 mg., 0.88 mmole) is added. After stirring for 1 hour, the bulk of the trifluoroacetic acid is removed at reduced pressure. The residue is treated with ether to afford a colorless solid which is collected by filtration (535 mg.).

The above solid (535 mg.) is dissolved in 80% acetic acid (20 ml.) and hydrogen sulfide is bubbled through the solution for 30 minutes. The resulting black mercuric sulfide is removed by filtration through Celite. The filtrate is refiltered through a Teflon millipore filter and concentrated at reduced pressure. The residue is chased twice with absolute ethanol, dissolved in water (8 ml.), treated with 1N hydrochloric acid (0.5 ml.), and lyophilized to give 0.33 g. of 1-[N-[(3S)-3-(benzoylamino)-2-mercapto-4-phenylbutyl]-L-alanyl]-L-proline (isomer A) as a colorless solid; m.p. 142°–176° (dec.); [α]$_D^{20}$= −89.6° (c=1.07, methanol). TLC (silica gel, n-butanol: acetic acid:water, 4:1:1) R$_f$=0.50.

Anal. calc'd. for $C_{25}H_{31}N_3O_4S \cdot HCl \cdot 0.38 H_2O$: C, 58.54; H, 6.44; N, 8.19; Cl, 6.91; S, 6.25; SH, 6.45. Found: C, 58.54; H, 6.44; N, 8.15; Cl, 6.91; S, 6.15; SH, 6.26.

EXAMPLE 2

1-[N-[(3S)-3-(Benzoylamino)-2-mercapto-4-phenyl-butyl]-L-alanyl]-L-proline, monohydrochloride (isomer B)

(a) 1-[N-[(3S)-3-(Benzoylamino)-2-[[(4-methoxyphenyl)methyl]thio]-4-phenylbutyl]-L-alanyl]-L-proline, 1,1-dimethylethyl ester (isomer B)

The partially purified mixture of diastereomers from Example 1(h), in which isomer B is the major component, is rechromatographed (flash, silica gel LPS-1; chloroform:methanol, 99:1) to give 0.26 g. of 1-[N-[(3S)-3-(benzoylamino)-2-[[(4-methoxyphenyl)methyl]thio]-4-phenylbutyl]-L-alanyl]-L-proline, 1,1-dimethylethyl ester (isomer B) as a colorless oil. TLC (silica gel; chloroform:methanol, 96:4) $R_f$=0.28.

(b) 1-[N-(3S)-3-(Benzoylamino)-2-mercapto-4-phenylbutyl]-L-alanyl]-L-proline, monohydrochloride isomer B)

A solution of the 1,1-dimethylethyl ester product from part (a) (0.26 g., 0.40 mmole) and anisole (0.5 ml.) in trifluoroacetic acid (9.5 ml.) is stirred at room temperature for one hour. After cooling to 0°, mercuric trifluoroacetate (171 mg., 1 eq.) is added. After stirring for 45 minutes, the bulk of the trifluoroacetic acid is removed at reduced pressure. The residue is treated with ether to give a colorless product which is collected by filtration (260 mg.).

The above colorless solid (260 mg.) is dissolved in 80% acetic (10 ml.) and hydrogen sulfide is bubbled through this solution for 30 minutes. The resulting black mercuric sulfide is removed by filtration through Celite. The product is refiltered (Teflon millipore) and the filtrate is concentrated at reduced pressure. The residue is chased once with absolute ethanol, dissolved in water (10 ml.), and then treated with 1N hydrochloric acid. The resulting solution is lyophilized to give a white fluffy solid (150 mg.). This material is dissolved in water (9 ml.), filtered (Teflon millipore), and relyophilized to a white fluffy solid which is then dried under vacuum over phosphorus pentoxide to give 136 mg. of 1-[N-[(3S)-3-(benzoylamino)-2-mercapto-4-phenylbutyl[-L-alanyl]-L-proline, monohydrochloride (isomer B); m.p. 147°–162°; $[\alpha]_D^{20}$= −64.5° (c=1.06, methanol). TLC (silica gel; n-butanol:acetic acid:water, 4:1:1) $R_f$=0.47.

Anal. calc'd. for $C_{25}H_{31}N_3O_4S \cdot HCl \cdot 1.0.36\ H_2O$: C, 58.58; H, 6.44; N, 8.20; S, 6.25; Cl, 6.92; SH, 6.45 Found: C, 58.58; H, 6.50; N, 8.14; S, 6.15; Cl, 6.71; SH, 6.10.

EXAMPLE 3

1-[N-[(3S)-3-(Benzoylamino)-2-mercapto-4-phenylbutyl]-L-lysyl]-L-proline, monohydrochloride (isomer A)

(a) 1-[$N^2$-[(Benzyloxy)carbonyl]-$N^6$-[(1,1-dimethylethoxy)carbonyl]-L-lysyl]-L-proline, 1,1-dimethylethyl ester A suspension of $N^2$-[(benzyloxy)carbonyl]-$N^6$-[(1,1-dimethylethoxy)carbonyl]-L-lysine, dicyclohexylamine salt (10.0 g., 17.8 mmole) in ethyl acetate (300 ml.) is extracted with 1N hydrochloric acid (three times). The organic phase is then washed with water and brine. After drying over anhydrous MgSO$_4$, the solvent is removed to give 5.81 g. of $N^2$-[(benzyloxy)carbonyl]-$N^6$-[(1,1-dimethylethoxy)carbonyl]-L-lysine as a pale yellow oil.

To a solution of $N^2$-[(benzyloxy)carbonyl]-$N^6$-](1,1-dimethylethoxy)carbonyl]-L-lysine (5.81 g., 15.3 mmole) and L-proline, 1,1-dimethylethyl ester (2.80 g., 16.4 mmole) in dry methylene chloride (70 ml.) is added 1-hydroxybenzotriazole (2.02 g., 14.95 mmole) and dicyclohexylcarbodiimide (3.09 g., 14.98 mmole). After stirring at room temperature for 15 hours, the mixture is filtered to remove the dicyclohexylurea. The filtrate is concentrated at reduced pressure and the residue is dissolved in ether and refiltered. The filtrate is washed with water (twice), 1N hydrochloric, acid (twice), 1N sodium bicarbonate, and brine. After drying over anhydrous MgSO$_4$, the solvent is removed at reduced pressure and the residue is flash chromatographed (silica gel LPS-1; hexane:ethyl acetate, 1:1) to give 8.13 g. of 1-[$N^2$-[(benzyloxy)carbonyl]-$N^6$-[(1,1-dimethylethoxy)carbonyl]-L-lysyl]-L-proline, 1,1-dimethylethyl ester as a colorless oil. TLC (silica gel; hexane:ethyl acetate, 1:1) $R_f$=0.21.

(b) 1-[$N^6$-[(1,1-Dimethylethoxy)carbonyl]-L-lysyl]-L-proline, 1,1-dimethylethyl ester A mixture of the 1,1-dimethylethyl ester product from part (a) (4.13 g., 7.73 mmole) and palladium hydroxide/carbon catalyst (400 mg.) in ethyl acetate (90 ml.) and ethanol (10 ml.) is stirred under a hydrogen atmosphere (balloon). The system is evacuated and refilled with fresh hydrogen every 30 minutes. After stirring for 3 hours, the catalyst is removed by filtration (Teflon millipore) and the filtrate is concentrated at reduced pressure to give 3.15 g. of 1-[$N^6$-](1,1-dimethylethoxy)carbonyl]-L-lysyl]-L-proline, 1,1-dimethylethyl ester as a colorless solid.

(c) 1-[N-[(3S)-3-(Benzoylamino)-2-[[(4-methoxyphenyl]methyl]thio]-4-phenylbutyl]-$N^6$-[(1,1-dimethylethoxy)carbonyl]-L-lysyl]-L-proline, 1,1-dimethylethyl ester (isomer A)

A mixture of (S)-$\beta$-(benzoylamino)-$\alpha$-[[(4-methoxyphenyl)methyl]thio]-benzenebutanal (isomer A) (0.59 g. 1.40 mmole), 1-[$N^6$-[(1,1-dimethylethoxy)carbonyl]-L-lysyl]-L-proline, 1,1-dimethylethyl ester (1.55 g., 3.88 mmole), and crushed 3A° molecular sieves (2.0 g.) in tetrahydrofuran (5 ml.) and absolute ethanol (5 ml.) is stirred at room temperature under argon. After stirring for 2 hours, sodium cyanoborohydride (0.27 g., 3 eq.) is added and stirring continued for 18 hours. The reaction mixture is filtered through Celite to remove the sieves. The filtrate is then diluted with ethyl acetate and washed with water, 1N hydrochloric acid (twice), 1N sodium bicarbonate, and brine. After drying over anhydrous MgSO$_4$, the solvent is removed at reduced pressure to give the desired product, a mixture of diastereomers, as a pale yellow oil. TLC (silica gel, benzene:acetone 4:1) isomer A at $R_f$=0.31, and isomer B at $R_f$=0.15. Repeated chromatography (flash, silica gel LPS-1; chloroform:methanol, 98:2; hexane:acetone, 65:35; benzene:acetone, 4:1; ethyl acetate:hexane, 6:4; ethyl acetate:hexane, 6:4) gives 0.41 g. of 1-[N-[(3S)-3-(benzoylamino)-2-[[(4-methoxyphenyl) methyl]thio]-4-phenylbutyl]-$N^6$-[(1,1-dimethylethoxy)carbonyl]-L-lysyl]-L-proline, 1,1-dimethylethyl ester (isomer A) as a colorless oil.

(d) 1-[N-[(3S)-3-(Benzoylamino)-2-mercapto-4-phenylbutyl]-L-lysyl]-L-proline, monohydrochloride (isomer A)

A solution of the 1,1-dimethylethyl ester product from part (c) (0.41 g., 0.51 mmole) and anisole (0.6 ml.) in trifluoroacetic acid (12 ml.) is stirred at room temperature for one hour. After cooling to 0°, mercuric trifluoroacetate (217 mg., 1.0 eq.) is added. After stirring for one hour at 0°, the bulk of the trifluoroacetic acid is removed at reduced pressure. The residue is treated with ether to give a colorless solid which is collected by filtration (0.49 g.).

This solid (0.49 g.) is dissolved in 80% acetic acid (17 ml.) and hydrogen sulfide is bubbled through the solution for 30 minutes. The resulting black mercuric sulfide is removed by filtration through Celite. The filtrate is refiltered (Teflon millipore) and then concentrated at reduced pressure. The residue is dissolved in water (10 ml.) and treated with 1N hydrochloric acid (1.5 ml.) and then lyophilized. The material is redissolved in water containing a small amount of hydrochloric acid and relyophilized. The material is finally lyophilized from water to give 290 mg. of 1-[N-[(3S)-3-(benzoylamino)-2-mercapto-4-phenylbutyl]-L-lysyl]-L-proline, monohydrochloride (isomer A); m.p. 157°-180°; $[\alpha]_D^{20} = -60.0°$ (c=1.15, methanol). TLC (silica gel; n-butanol: acetic acid:water 4:1:1) $R_f$=0.16.

Anal.calc'd. for $C_{28}H_{38}N_4O_4S \cdot 2HCl \cdot 1.0\ H_2O$: C, 54.45; H, 6.85; N, 9.07; S, 5.19; Cl, 11.48; SH, 5.35 Found: C, 54,35; H, 6.67; N, 8.97; S, 5.20 Cl, 11.36; SH, 5.23.

EXAMPLES 4-42

Following the procedure of Examples 1 to 3 to carboxylic acid methyl ester shown in Col. I is reacted with (4-methoxyphenyl)methyl disulfide to yield the carboxylic acid methyl ester shown in Col. II. This is then converted to the corresponding alcohol and then the aldehyde shown in Col. III. The aldehyde is then reacted with the peptidyl ester shown in Col. IV to yield the protected sulfide product shown in Col. V. Removal of the S-protecting group and the carboxylic acid ester group yields the final product shown in Col. VI.

Col. I

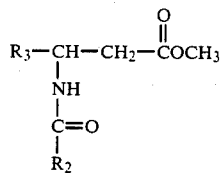

Col. II

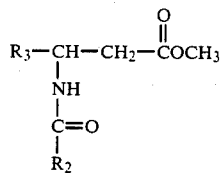

-continued

Col. III

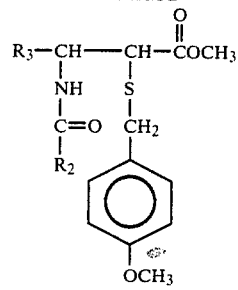

Col. IV

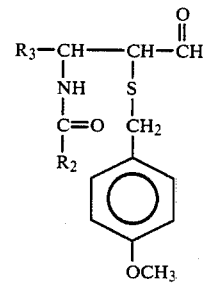

Col. V

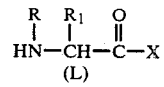

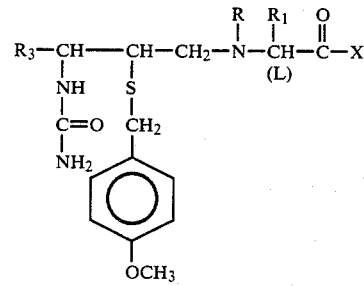

Col. VI

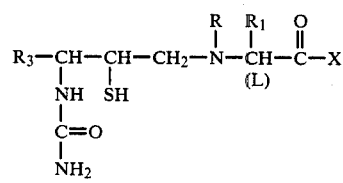

| Example | R₃ | R₂ | R₁ | X | R |
|---|---|---|---|---|---|
| 4 | PhCH₂— | Ph | H— | ![structure with benzothiophene, —N—CH₂—, CH—COOC(CH₃)₃ (L), H] | H₃C— |
| 5 | PhCH₂— | Ph | H— | ![piperidine-type, —N—, CH—COOC(CH₃)₃ (L), H] | H₃C— |
| 6 | H₃C— | Ph | PhCH₂— | —NH—CH—COOC(CH₃)₃ (L) / CH₂—CH(CH₃)₂ | H— |
| 7 | PhCH₂— | Ph | H₃C— | ![benzothiophene, —N—CH₂—, CH—COOC(CH₃)₃ (L), H] | H— |
| 8 | PhCH₂— | Ph | H— | ![dithiolane, —N—CH₂—, CH—COOC(CH₃)₃ (L), H] | cyclohexyl |

-continued

| Example | R₃ | R₂ | R₁ | X | R |
|---------|----|----|----|---|---|
| 9 | 4-F-C₆H₄-CH₂- | 4-F-C₆H₄-CH₂- | H- | -N(H)-CH(CH₂-Cy)-CH₂-CH(COOC(CH₃)₃)- (L) | C₆H₅-CH₂- |
| 10 | C₆H₅-(CH₂)₄- | 4-CH₃-C₆H₄- | H- | -N(H)-CH(CH₂-(2-CH₃O-C₆H₄))-CH₂-CH(COOC(CH₃)₃)- (L) | H₃C- |
| 11 | 2-thienyl-CH₂- | C₆H₅-(CH₂)₂- | H₃C- | 1,2,3,4-tetrahydroisoquinoline-3-COOC(CH₃)₃ (L) | H₃C- |
| 12 | 4-pyridyl-CH₂- | C₆H₅- | H₃C- | -N(H)-CH(COOCH(C₆H₅)₂)-(CH₂)₃- (L) | H- |
| 13 | 4-CH₃O-C₆H₄-CH₂- | C₆H₅- | H₃C- | -N(H)-CH(COOC(CH₃)₃)-(CH₂)₃- (L) | H- |

-continued

| Example | R₃ | R₂ | R₁ | X | R |
|---|---|---|---|---|---|
| 14 | benzyl (PhCH₂–) | phenyl | H– | 4-fluorophenoxymethyl-CH₂-CH(COOC(CH₃)₃)-N< (L), H | H₃C– |
| 15 | benzyl (PhCH₂–) | phenyl | H₃C– | 4-fluorophenoxymethyl-CH₂-CH(COOC(CH₃)₃)-N< (L), H | H– |
| 16 | benzyl (PhCH₂–) | phenyl | H₃C– | phenyl-CH(CH₂-N<)-CH(COOC(CH₃)₃)(L), H | H– |
| 17 | benzyl (PhCH₂–) | phenyl | H₃C– | cyclohexyl-CH(CH₂-N<)-CH(COOC(CH₃)₃)(L), H | H– |

-continued

| Example | R₃ | R₂ | R₁ | X | R |
|---|---|---|---|---|---|
| 18 | H₃C— | PhCH₂— | PhCH₂— | PhCH₂—S—CH(CH₂N—)—CH₂—CH(COOC(CH₃)₃)(H) (L) | H— |
| 19 | 2-thienyl-CH₂— | 4-Cl-C₆H₄— | H— | Ph—O—CH(CH₂N—)—CH₂—CH(COOC(CH₃)₃)(H) (L) | H— |
| 20 | H₃C—CH₂— | Ph(CH₂)₂— | H₂C=OH-CH₂C— | 2-(PhCH₂)-C₆H₄—CH(CH₂N—)—CH(COOC(CH₃)₃)(H) (L) | H— |
| 21 | PhCH₂— | Ph— | HN=C(NHNO₂)—HN—(H₂C)₃— | PhCH₂—OCH(OCH₃)—CH₂N—/CH(COOCH₂Ph)(H) with COOC(CH₃)₃ (L) | H— |
| 22 | PhCH₂— | 3-pyridyl— | PhCH₂OCOCHN(H₂C)₄— | thiazolidine-CH(COOC(CH₃)₃)(H) (L) | H— |

-continued

| Example | R₃ | R₂ | R₁ | X | R |
|---|---|---|---|---|---|
| 23 | benzyl (PhCH₂–) | phenyl | O=C(–)–NHCH(CH₂OCH₂)S–(CH₂)₂– (phenyl) | cyclic: –N–CH₂CH₂CH₂–CH(COOCH)(L)–H, fused with (phenyl)₂ | H– |
| 24 | benzyl (PhCH₂–) | phenyl | (4-H₃C–C₆H₄–O–CH)₂(phenyl)₂ | PhCH₂–C(=N–N)–CH(COOCH)(L)–H, (phenyl)₂ | H– |
| 25 | benzyl (PhCH₂–) | phenyl | (H₂C–C₆H₃)(HCO–)(phenyl)₂–(HCO–)₂ | –N–CH₂–CH=CH–CH(COOCH)(L)–H, (phenyl)₂ | H– |
| 26 | –(CH₂)₃–phenyl | phenyl | (N=CH–CH₂–)(phenyl)₂ | spiro dioxolane –N–CH₂–CH(COOC(CH₃)₃)–H | H– |
| 27 | benzyl (PhCH₂–) | 4-methylphenyl (H₃C–C₆H₄–) | H₂C–CH=N–H (indole-linked) | piperidine –N–CH(COOCH)(L)–H, (phenyl)₂ | H– |

-continued

| Example | R₃ | R₂ | R₁ | X | R |
|---|---|---|---|---|---|
| 28 | C₆H₅(CH₂)₂— | C₆H₅CH₂— | H₃C—S—(H₂C)₂— | (phenylthio-substituted chain with COOC(CH₃)₃ (L), H) | H— |
| 29 | C₆H₅(H₂C)₄NHCOH₂C— (with C=O) | C₆H₅— | H₃C— | (chain with COOC(CH₃)₃ (L), H) | H— |
| 30 | indol-3-ylmethyl (H₂C— attached to indole N—H) | C₆H₅— | H₃C— | —N₃ substituted chain with COOC(CH₃)₃ (L), H | H— |
| 31 | C₆H₅CH₂— | C₆H₅— | H₃C— | —N—C₆H₅ (anilino) | H— |
| 32 | H₃C— | C₆H₅— | H— | —NH—CH(CH₂CH(CH₃)₂)—COOC(CH₃)₃ (L) | H₃C— |
| 33 | H₅C₂— | 3-pyridyl | C₆H₅CH₂— | —NH—CH(CH₂-indol-3-yl)—COOC(CH₃)₃ (L) | H— |

-continued

| Example | $R_3$ | $R_2$ | $R_1$ | X | R |
|---|---|---|---|---|---|
| 34 | $H_3C-$ | –⟨phenyl⟩ | $H_3C-$ | $-NH-CH(CH_2-C_6H_5)-COOC(CH_3)_3$ (L) | H– |
| 35 | $H_3C-$ | –⟨phenyl⟩ | $C_6H_5-CH_2-$ | $-NH-CH(CH_2-C_6H_4-OC(CH_3)_3)-COOC(CH_3)_3$ (L) (with $(\ )_2$) | H– |
| 36 | $H_3C-$ | –⟨phenyl⟩ | $H_3C-$ | $-NH-CH(CH_2-CH=N-OCH(C_6H_5)_2)-COOC(CH_3)_3$ (L) | H– |
| 37 | $-CH_2-C_6H_5$ | –⟨phenyl⟩ | $H_3C-$ | pyrrolidine-$C(=O)-CH(CH(CH_3)_2)-O-C(=O)-C_2H_5$ (L) | H– |
| 38 | $-CH_2-C_6H_5$ | –⟨phenyl⟩ | $H_3C-$ | piperidine(cyclohexyl)-$C(=O)-CH(C_6H_{11})-O-C(=O)-C_2H_5$ (L) | H– |

-continued

| Example | R₃ | R₂ | R₁ | X | R |
|---|---|---|---|---|---|
| 39 | C₆H₅-CH₂- | C₆H₅ | H- | phenyl-thio-methyl substituted pyrrolidine with -C(=O)-O-CH(CH₃)-O-C(=O)-C₂H₅, CH(CH₃)₂ (L) | H₃C- |
| 40 | C₆H₅-CH₂- | C₆H₅ | H₃C- | pyrrolidine-COOC₂H₅ (L) | H- |
| 41 | C₆H₅-CH₂- | C₆H₅ | H- | phenyl-thio-methyl pyrrolidine-COOC₂H₅ (L) | H₃C- |
| 42 | C₆H₅-CH₂- | C₆H₅ | H₃C- | dithiolane-substituted pyrrolidine-COOC₃H₇ (L) | H- |

The R₁ protecting groups in Examples 20 to 26, the R₃ protecting group in Example 29, and R₅ protecting group in Example 35 are removed as the last step in the synthesis. The 4-azidoproline of Example 30 when treated with the reducing agent will yield a 4-aminoproline product. The R₆ ester groups shown in Examples 37 to 42 are not removed.

EXAMPLES 43–55

1-[N-[(3S)-3-(Benzoylamino)-2-[[(4-methoxyphenyl)-methyl]thio]-4-phenylbutyl]-L-alanyl]-L-proline (isomer A) is treated with the reagent listed below in Col. I to give the product shown in Col. II.

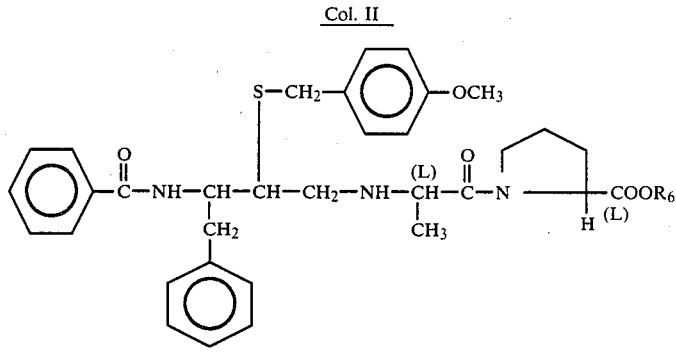

Col. II

Deprotection by treatment with mercuric trifluoroacetate yields the desired final product.

| Example | Col. I | R₆ |
|---|---|---|
| 43 | Cl—CH(C₆H₁₁)—O—C(O)—C₂H₅ | —CH(C₆H₁₁)—O—C(O)—C₂H₅ |
| 44 | Cl—CH(CH(CH₃)₂)—O—C(O)—C₂H₅ | —CH(CH(CH₃)₂)—O—C(O)—C₂H₅ |
| 45 | Cl—CH₂—O—C(O)—C(CH₃)₃ | —CH₂—O—C(O)—C(CH₃)₃ |
| 46 | Br—CH₂—O—C(O)—CH₃ | —CH₂—O—C(O)—CH₃ |
| 47 | Cl—CH₂—O—C(O)—C₆H₅ | —CH₂—O—C(O)—C₆H₅ |
| 48 | I—CH₂—C(O)—O—C(CH₃)₃ | —CH₂—C(O)—O—C(CH₃)₃ |
| 49 | I—C(CH₃)₂—C(O)—O—CH₃ | —C(CH₃)₂—C(O)—O—CH₃ |
| 50 | CH(OH)—[CH₂—O—CH(C₆H₅)₂]₂ | —CH(CH₂—OH)₂ |
| 51 | CH₂(OH)—CH(O—CH(C₆H₅)₂)—CH₂(O—CH(C₆H₅)₂) | —CH₂—CH(OH)—CH₂(OH) |
| 52 | HO—CH₂—CH₂—N(CH₃)₂ | —CH₂—CH₂—N(CH₃)₂ |

-continued

| Example | Col. I | R$_6$ |
|---------|--------|-------|
| 53 | HO—(CH$_2$)$_2$—[pyridine] | —(CH$_2$)$_2$—[pyridine] |
| 54 | HO—(CH$_2$)$_3$—[pyridine] | —(CH$_2$)$_3$—[pyridine] |
| 55 | HO—(CH$_2$)$_2$—[pyridine] | —(CH$_2$)$_2$—[pyridine] |

In the case of Examples 50 to 55, the reaction with the reagent listed in Col. I is performed in the presence of a coupling agent such as dicyclohexylcarbodiimide.

EXAMPLE 56

1-[N-[(3S)-3-(Benzoylamino)-2-mercapto-4-phenylbutyl]-L-alanyl]-L-proline, sodium salt (isomer A)

1-[N-[(3S)-3-(Benzoylamino)-2-mercapto-4-phenylbutyl]-L-alanyl]-L-proline (isomer A) (1 mmole) is dissolved in water (50 ml.). Aqueous sodium bicarbonate (0.1N, 20 ml.) is added and the aqueous solution is lyophilized. It is then dissolved in water (10 ml.) and applied on a column (5 cm. × 60 cm.) of Sephadex chromatography gel G-10 and eluted with water. Fractions containing the desired product are pooled and lyophilized to give 1-[N-[(3S)-3-(benzoylamino)-2-mercapto-4-phenylbutyl]-L-alanyl]-L-proline, sodium salt (isomer A).

EXAMPLE 57

1000 tablets each containing the following ingredients

| | |
|---|---|
| 1-[N—[(3S)-3-(Benzoylamino)-2-mercapto-4-phenylbutyl]-L-alanyl]-L-proline, sodium salt (isomer A) | 100 mg |
| Corn starch | 50 mg. |
| Gelatin | 7.5 mg. |
| Avicel(microcrystalline cellulose) | 25 mg. |
| Magnesium stearate | 2.5 mg. |
| | 185 mg. | are prepared from sufficient bulk quantities by mixing the 1-[N-[(3S)-3-(benzoylamino)-2-mercapto-4-phenylbutyl]-L-alanyl)-L-proline, sodium salt (isomer A) and corn starch with an aqueous solution of the gelatin. The mixture is dried and ground to a fine powder. The Avicel and then the magnesium stearate are admixed with granulation. This mixture is then compressed in a tablet press to form 1000 tablets each containing 100 mg. of active ingredient.

In a similar manner, tablets containing 100 mg. of the product of any of Examples 1 to 55 can be prepared.

A similar procedure can be employed to form tablets containing 50 mg. of active ingredient.

EXAMPLE 58

Two piece #1 gelatin capsules each containing 50 mg. of 1-[N-[(3S)-3-benzoylamino)-2-mercapto-4-phenylbutyl]-L-lysyl]-L-proline, monohydrochloride (isomer A) are filled with a mixture of the following ingredients:

| | |
|---|---|
| 1-[N—[(3S)-3-(benzoylamino)-2-mercapto-4-phenylbutyl]-L-lysyl]-L-proline, monohydrochloride (isomer A) | 50 mg. |
| Magnesium stearate | 7 mg. |
| Lactose | 193 mg. |
| | 250 mg. |

In a similar manner capsules containing 50 mg. of the product of any of Examples 1, 2 and 4 to 56 can be prepared.

EXAMPLE 59

An injectable solution is prepared as follows:

| | |
|---|---|
| 1-[N—[(3S)-3-(Benzoylamino)-2-mercapto-4-phenylbutyl]-L-alanyl]-L-proline, sodium salt (isomer A) | 500 g. |
| Methyl paraben | 5 g. |
| Propyl paraben | 1 g. |
| Sodium chloride | 25 g. |
| Water for injection | 5 l |

The active substance, preservatives, and sodium chloride are dissolved in 3 liters of water for injection and then the volume is brought up to 5 liters. The solution is filtered through a sterile filter and aseptically filled into presterilized vials which are closes with presterilized rubber closures. Each vial contains 5 ml. of solution in a concentration of 100 mg. of active ingredient per ml. of solution for injection.

In a similar manner, an injectable solution containing 100 mg. of active ingredient per ml. of solution can be prepared for the product of any of Examples 1 to 56.

EXAMPLE 60

1000 tablets each containing the following ingredients:

| | |
|---|---|
| 1-[N—[(3S)-3-(Benzoylamino)-2-mercapto-4-phenylbutyl]-L-alanyl]-L-proline, sodium salt (isomer A) | 100 mg. |
| Avicel | 100 mg. |
| Hydrochlorothiazide | 12.5 mg. |

-continued

| Lactose | 113 mg. |
| --- | --- |
| Cornstarch | 17.5 mg. |
| Stearic Acid | 7 mg. |
| | 350 mg. | are prepared from sufficient bulk quantities by slugging the 1-[N-[(3S)-3-(benzoylamino)-2-mercapto-4-phenyl-butyl]-L-alanyl]-L-proline, sodium salt (isomer A), Avicel, and a portion of the stearic acid. The slugs are ground and passed through a #2 screen, then mixed with the hydrochlorothiazide, lactose, cornstarch, and remainder of the stearic acid. The mixture is compressed into 350 mg. capsule shaped tablets in a tablet press. The tablets are scored for dividing in half.

In a similar manner, tablets can be prepared containing 100 mg. of the product of any of Examples 1 to 55.

What is claimed is:

1. A compound of the formula

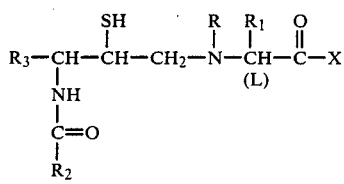

or a pharmaceutically acceptable salt thereof wherein X is

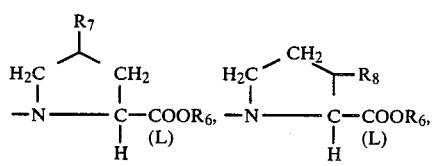

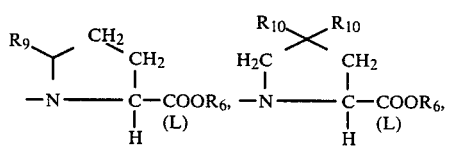

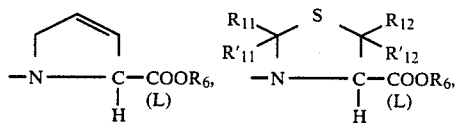

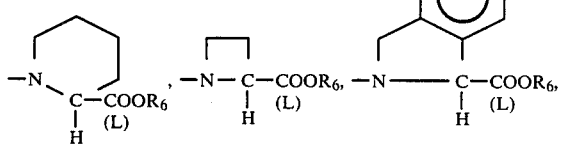

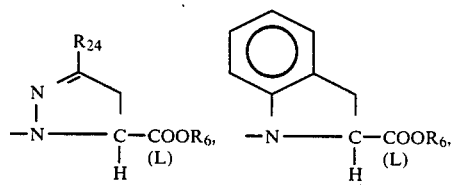

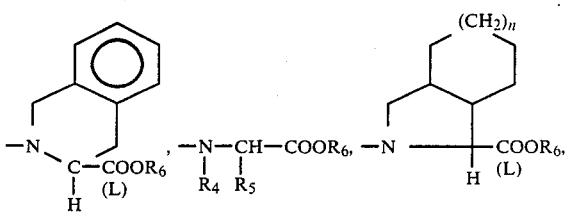

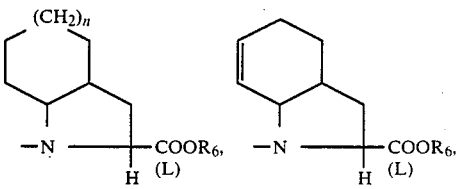

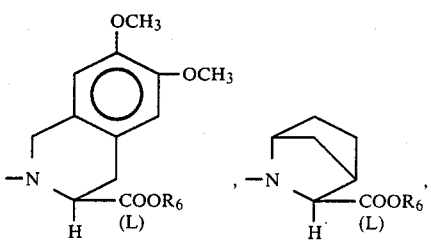

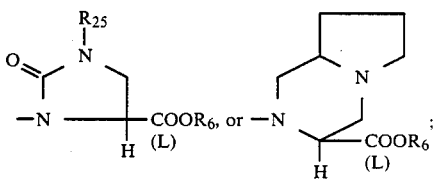

n is zero, one, or two.

$R_{25}$ is lower alkyl of 1 to 4 carbons or

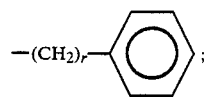

R is hydrogen, lower alkyl, cycloalkyl,

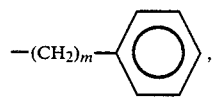

—(CH$_2$)$_2$—NH$_2$, —(CH$_2$)$_3$—NH$_2$, —(CH$_2$)$_4$—NH$_2$, —(CH$_2$)$_2$—OH, —(CH$_2$)$_3$—OH, —(CH$_2$)$_4$—OH, —(CH$_2$)$_2$—SH, —(CH$_2$)$_3$—SH, or —(CH$_2$)$_4$—SH;

$R_1$ is hydrogen, lower alkyl, halo substituted lower alkyl,

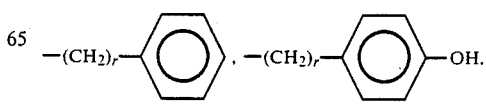

-continued

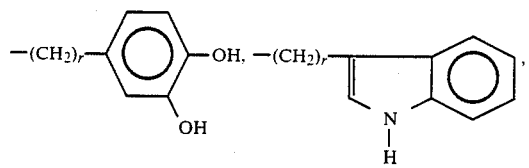

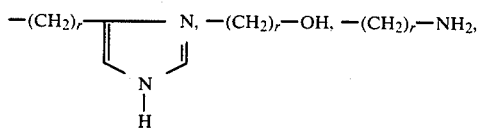

—(CH$_2$)$_r$—SH, —(CH$_2$)$_r$—S—lower alkyl,

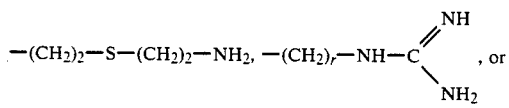

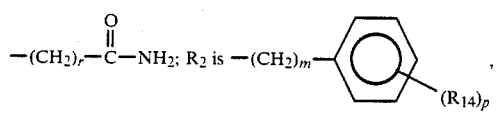

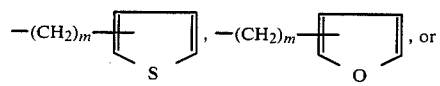

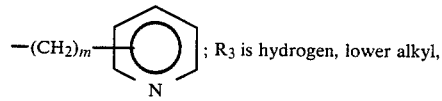

halo substituted lower alkyl, —(CH$_2$)$_m$—cycloalkyl,

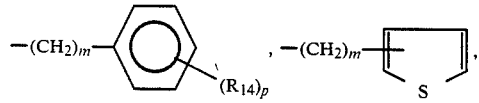

—(CH$_2$)$_r$—OH, —(CH$_2$)$_r$— 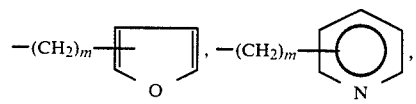 N, —(CH$_2$)$_r$—NH$_2$,

—(CH$_2$)$_r$—SH, —(CH$_2$)$_r$—S—lower alkyl,

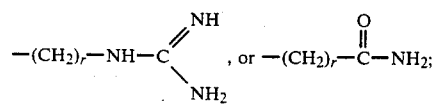

-continued

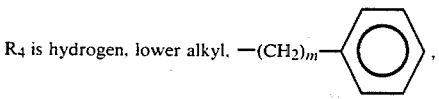

—(CH$_2$)$_m$—cycloalkyl, 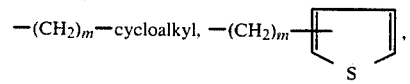

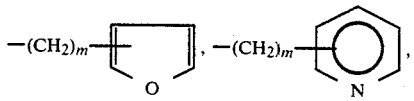

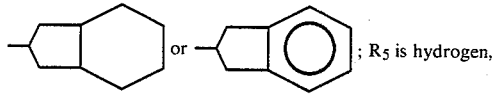

lower alkyl, 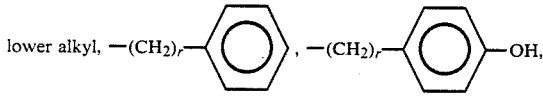

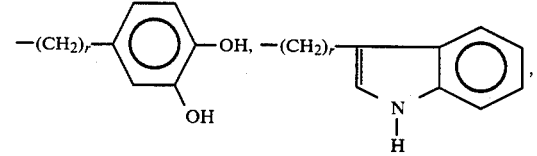

—(CH$_2$)$_r$— 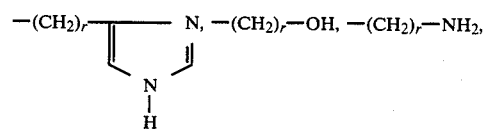 N, —(CH$_2$)$_r$—OH, —(CH$_2$)$_r$—NH$_2$,

—(CH$_2$)$_r$—SH, —(CH$_2$)$_r$—S—lower alkyl,

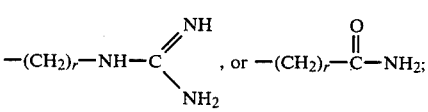

r is an integer from 1 to 4; R$_7$ is hydrogen, lower alkyl, halogen, hydroxy, —NH—C(=O)—lower alkyl, amino, —NR$_{19}$R$_{20}$,

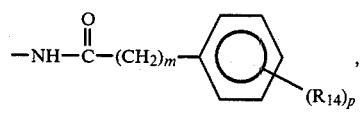

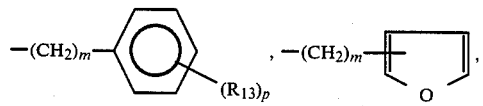

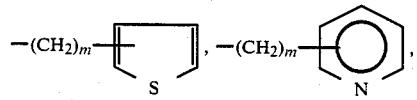

a 1- or 2-naphthyl of the formula

-continued

—(CH₂)ₘ—
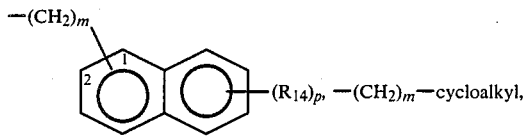
(R₁₄)ₚ, —(CH₂)ₘ—cycloalkyl,

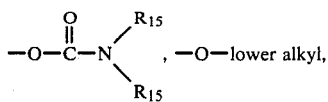
, —O—lower alkyl,

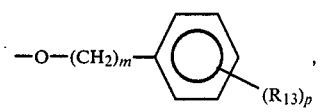
, a 1- or 2-naphthyloxy of the formula

—O—(CH₂)ₘ—
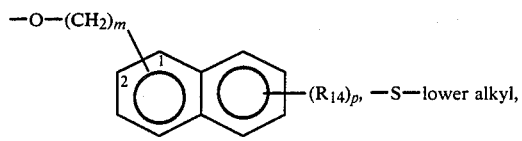
(R₁₄)ₚ, —S—lower alkyl,

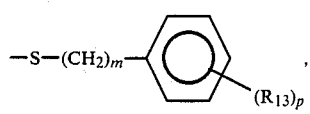
, or a 1- or 2-naphthylthio of the formula

—S—(CH₂)ₘ—
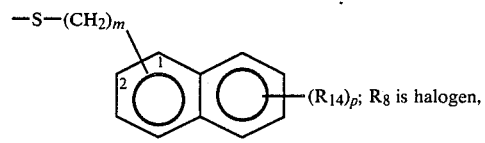
(R₁₄)ₚ; R₈ is halogen,

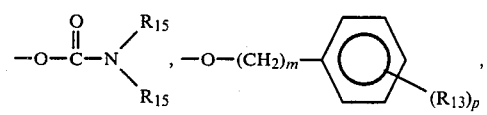
—O—lower alkyl, a 1- or 2-naphthyloxy of the formula

—O—(CH₂)ₘ—
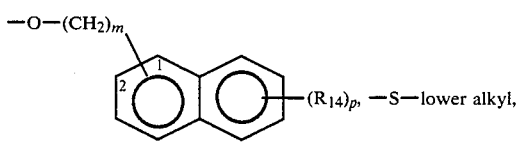
(R₁₄)ₚ, —S—lower alkyl,

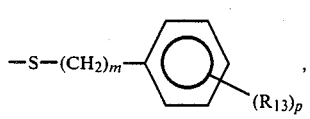
, or a 1- or 2-naphthylthio of the formula

—S—(CH₂)ₘ—
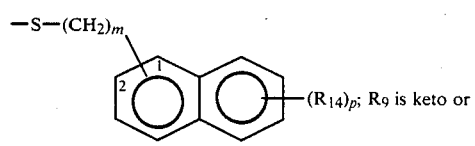
(R₁₄)ₚ; R₉ is keto or

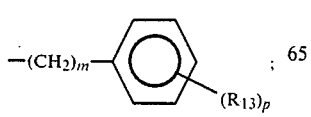
;

$R_{10}$ is halogen or —Y—$R_{16}$;
$R_{11}$, $R'_{11}$, $R_{12}$ and $R'_{12}$ are independently selected from hydrogen and lower alkyl or $R'_{11}$, $R_{12}$ and $R'_{12}$ are hydrogen and $R_{11}$ is

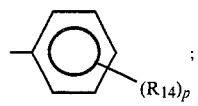
;

$R_{13}$ is hydrogen, lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenoxy, phenylthio, or phenylmethyl;
$R_{14}$ is hydrogen, lower alkyl of 1 to 4 carbons, lower alkoxy of 1 to 4 carbons, lower alkylthio of 1 to 4 carbons, chloro, bromo, fluoro, trifluoromethyl, or hydroxy;
m is zero, one, two, three, or four;
p is one, two or three provided that p is more than one only if $R_{13}$ or $R_{14}$ is hydrogen, methyl, methoxy, chloro, or fluoro;
$R_{15}$ is hydrogen or lower alkyl of 1 to 4 carbons;
Y is oxygen or sulfur;
$R_{16}$ is lower alkyl of 1 to 4 carbons,

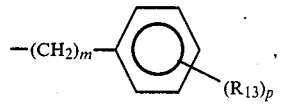
, or the $R_{16}$ groups join to complete an unsubstituted 5- or 6-membered ring or said ring in which one or more of the carbons has a lower alkyl of 1 to 4 carbons or a di(lower alkyl of 1 to 4 carbons) substituent;
$R_{19}$ is lower alkyl, benzyl, or phenethyl;
$R_{20}$ is hydrogen, lower alkyl, benzyl or phenethyl;
$R_6$ is hydrogen, lower alkyl, p-methoxybenzyl, benzhydryl,

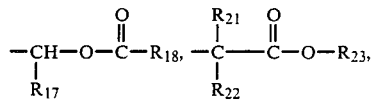
,

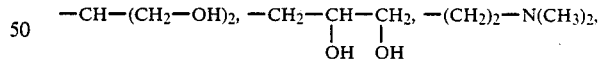

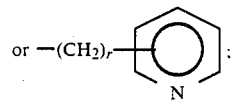

$R_{17}$ is hydrogen, lower alkyl, cycloalkyl or phenyl;
$R_{18}$ is hydrogen, lower alkyl, lower alkoxy, phenyl, or $R_{17}$ and $R_{18}$ taken together are —(CH₂)₂—, —(CH₂)₃—, —CH=CH, or

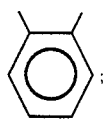
;

$R_{24}$ is hydrogen, lower alkyl,

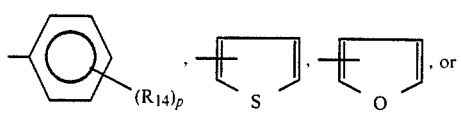

$R_{21}$ and $R_{22}$ are independently selected from the group consisting of hydrogen and lower alkyl; and $R_{23}$ is lower alkyl.

2. A compound of claim 1 wherein:
R is hydrogen, straight or branched chain lower alkyl of 1 to 4 carbons, or phenyl;
$R_1$ is hydrogen, straight or branched chain lower alkyl of 1 to 4 carbons, $CF_3$, $-(CH_2)_r-NH_2$,

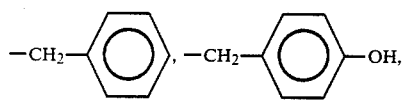

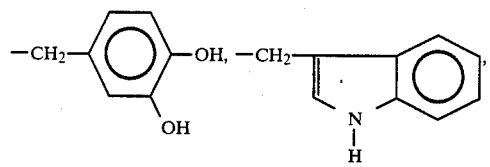

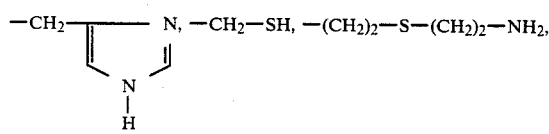

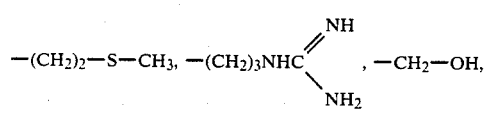

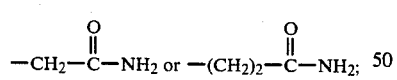

$R_4$ is hydrogen, cyclohexyl, or phenyl;
$R_5$ is hydrogen, straight or branched chain lower alkyl of 1 to 4 carbons,

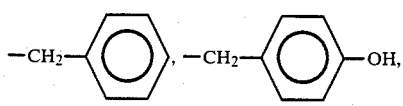

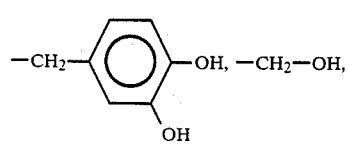

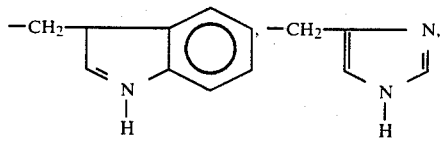

$-(CH_2)_4-NH_2$, $-CH_2-SH$, $-(CH_2)_2-S-CH_3$,

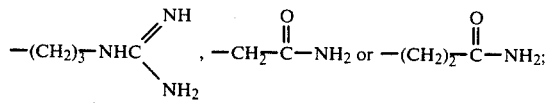

$R_6$ is hydrogen, straight or branched chain lower alkyl of 1 to 4 carbons, an alkali metal salt ion,

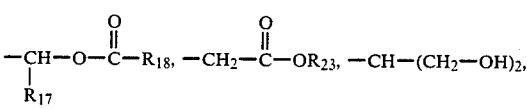

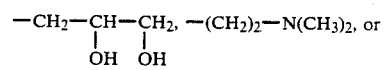

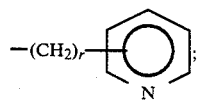

$R_{17}$ is hydrogen, straight or branched chain lower alkyl of 1 to 4 carbons, or cyclohexyl;
$R_{18}$ is straight or branched chain lower alkyl of 1 to 4 carbons or phenyl;
$R_{23}$ is straight or branched chain lower alkyl of 1 to 4 carbons;
$R_2$ is

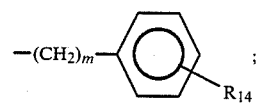

$R_3$ is straight or branched chain lower alkyl of 1 to 4 carbons, $-(CH_2)_r-NH_2$,

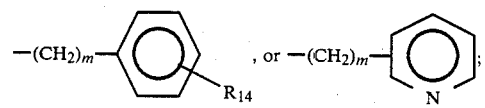

$R_7$ is hydrogen, hydroxy, straight or branched chain lower alkyl of 1 to 4 carbons, cyclohexyl, amino, —O—lower alkyl wherein lower alkyl is straight or branched chain of 1 to 4 carbons,

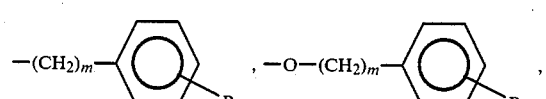

1-naphthyloxy, 2-naphthyloxy, —S—lower alkyl wherein lower alkyl is straight or branched chain of 1 to 4 carbons,

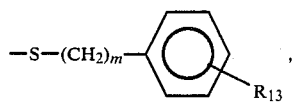

1-naphthylthio, or 2-naphthylthio;

$R_8$ is —O—lower alkyl, —S—lower alkyl,

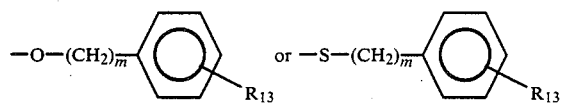

wherein lower alkyl is straight or branched chain of 1 to 4 carbons, $R_9$ is phenyl, 2-hydroxyphenyl or 4-hydroxyphenyl;

$R_{10}$ are both fluoro, both chloro, or both —Y—$R_{16}$;

Y is O or S;

$R_{16}$ is straight or branched chain lower alkyl of 1 to 4 carbons or the $R_{16}$ groups join to complete an unsubstituted 5- or 6-membered ring or said ring in which one or more of the available carbons has a methyl or dimethyl substituent;

$R_{11}$, $R_{11}'$, $R_{12}$ and $R_{12}'$ are all hydrogen or $R_{11}$ is phenyl, 2-hydroxyphenyl, or 4-hydroxyphenyl and $R_{11}'$, $R_{12}$ and $R_{12}'$ are all hydrogen;

r is an integer from 1 to 4;

m is zero, one, or two;

$R_{13}$ is hydrogen, methyl, methoxy, methylthio, chloro, bromo, fluoro, or hydroxy;

$R_{14}$ is hydrogen, methyl, methoxy, methylthio, chloro, bromo, fluoro, or hydroxy; and $R_{24}$ is phenyl.

3. A compound of claim 2 wherein:

X is

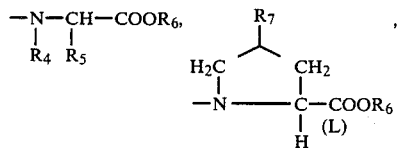

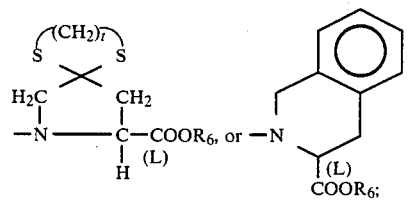

R is hydrogen or methyl;

$R_1$ is hydrogen, methyl, or —(CH$_2$)$_4$—NH$_2$;

$R_6$ is hydrogen, straight or branched chain lower alkyl or 1 to 4 carbons, or an alkali metal salt ion;

$R_4$ is cyclohexyl or phenyl and $R_5$ is hydrogen or $R_4$ is hydrogen and $R_5$ is methyl, —CH$_2$—CH(CH$_3$)$_2$,

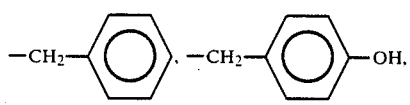

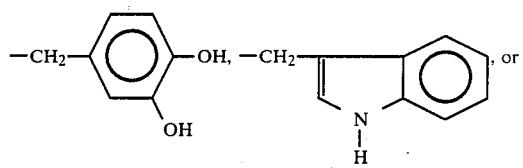

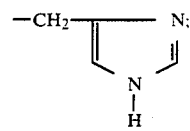

$R_7$ is hydrogen, cyclohexyl, lower alkoxy of 1 to 4 carbons,

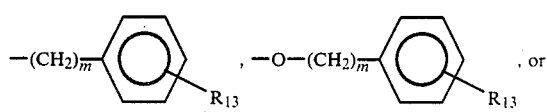

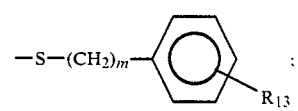

m is zero, one or two;

$R_{13}$ is hydrogen, methyl, methoxy, methylthio, chloro, bromo, fluoro, or hydroxy; and t is 2 or 3.

4. A compound of claim 3 wherein

X is

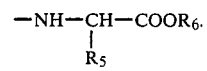

5. A compound of claim 3 wherein

X is

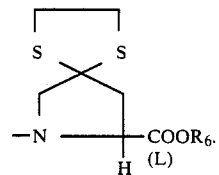

6. A compound of claim 3 wherein

X is

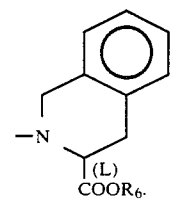

7. A compound of claim 3 wherein

X is

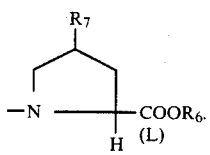

8. A compound of claim 7 wherein
R$_2$ is phenyl; and
R$_3$ is

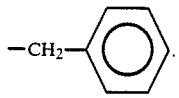

9. A compound of claim 8 wherein
R$_7$ is hydrogen.

10. A compound of claim 9 wherein
R$_6$ is hydrogen;
R is hydrogen; and
R$_1$ is methyl.

11. The compound of claim 10, 1-[N-[(3S)-3 -(benzoylamino)-2-mercapto-4-phenylbutyl]-L-alanyl]-L-proline (isomer A).

12. The compound of claim 10, 1-[N-[(3S)-3-(benzoylamino)-2-mercapto-4-phenylbutyl]-L-alanyl]-L-proline (isomer B).

13. A compound of claim 9 wherein
R$_6$ is hydrogen;
R is hydrogen; and
R$_1$ is —(CH$_2$)$_4$—NH$_2$.

14. The compound of claim 13, 1-[N-[(3S)-3-(benzoylamino)-2-mercapto-4-phenylbutyl]-L-lysyl]-L-proline, monohydrochloride (isomer A).

15. A pharmaceutical composition useful for treating hypertension comprising a pharmaceutically acceptable carrier and a hypotensive compound of the formula

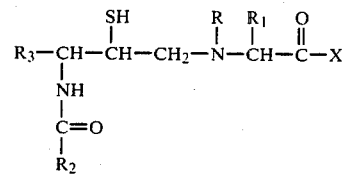

wherein R, R$_1$, R$_2$, R$_3$ and X are as defined in claim 1.

16. The method of treating hypertension in a mammalian host which comprises administering an effective amount of the composition of claim 15.

17. A pharmaceutical composition useful as an analgesic comprising a pharmaceutically acceptable carrier and an enkephalinase inhibiting compound of the formula

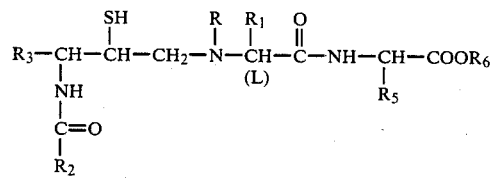

wherein R, R$_1$, R$_2$, R$_3$, R$_5$ and R$_6$ are as defined in claim 1.

18. The method of relieving pain in a mammalian host which comprises administering an effective amount of the composition of claim 17.

* * * * *